(12) United States Patent
Edwards et al.

(10) Patent No.: US 9,931,319 B2
(45) Date of Patent: Apr. 3, 2018

(54) CARBOXAMIDE DERIVATIVES

(71) Applicants: Anne-Marie Edwards, Surrey (GB); Mahbub Ahmed, Horsham (GB); Robert Alexander Pulz, Basel (CH); Lisa Ann Rooney, Surrey (GB); Nichola Smith, Cambridge, MA (US); Thomas Josef Troxler, Wahlen b. Laufen (CH)

(72) Inventors: Anne-Marie Edwards, Surrey (GB); Mahbub Ahmed, Horsham (GB); Robert Alexander Pulz, Basel (CH); Lisa Ann Rooney, Surrey (GB); Nichola Smith, Cambridge, MA (US); Thomas Josef Troxler, Wahlen b. Laufen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/197,091

(22) Filed: Jun. 29, 2016

(65) Prior Publication Data

US 2017/0000770 A1    Jan. 5, 2017

Related U.S. Application Data

(63) Continuation of application No. 14/711,693, filed on May 13, 2015, now Pat. No. 9,403,833.

(30) Foreign Application Priority Data

May 14, 2014   (EP) ..................................... 14168319

(51) Int. Cl.
| | |
|---|---|
| *A61K 31/4192* | (2006.01) |
| *A61K 31/55* | (2006.01) |
| *C07D 487/04* | (2006.01) |
| *C07D 403/12* | (2006.01) |
| *C07D 413/14* | (2006.01) |
| *C07D 413/12* | (2006.01) |

(52) U.S. Cl.
CPC .......... *A61K 31/4192* (2013.01); *A61K 31/55* (2013.01); *C07D 403/12* (2013.01); *C07D 413/12* (2013.01); *C07D 413/14* (2013.01); *C07D 487/04* (2013.01)

(58) Field of Classification Search
None
See application file for complete search history.

(56) References Cited

U.S. PATENT DOCUMENTS

| | | |
|---|---|---|
| 7,354,722 B1 | 4/2008 | Thomsen et al. |
| 9,403,810 B2 | 8/2016 | Bala et al. |
| 9,403,833 B2 | 8/2016 | Edwards et al. |
| 2006/0223873 A1 | 10/2006 | Shaw et al. |
| 2009/0163545 A1 | 6/2009 | Goldfarb et al. |
| 2015/0329549 A1 | 11/2015 | Edwards et al. |

FOREIGN PATENT DOCUMENTS

| | | |
|---|---|---|
| GB | 1696383 | 8/1981 |
| WO | 2004106306 A1 | 12/2004 |
| WO | 2005030128 A2 | 4/2005 |
| WO | 2008121861 A2 | 10/2008 |
| WO | 2009011850 A2 | 1/2009 |
| WO | 2009016241 A1 | 2/2009 |
| WO | 2011151361 A1 | 12/2011 |

OTHER PUBLICATIONS

International Search Report and Written Opinion for International Application No. PCT/US2015/030817 dated Jun. 25, 2015. 17 pages.
Database PubChem Compound. Compound Summary for: CID 3245828. http://pubchem.ncbi.nlm.nih.gov/summary.cgi?cid=3245828. XP002729647. Published Aug. 16, 2005. Printed Nov. 9, 2014. 9 pages.
Database PubChem Compound. Compound Summary for: CID 3241509. http://pubchemncbi.nlm.nih.gov/summary/summary.cgi?cid=3241509. XP002729648. Published Aug. 16, 2005. Printed Nov. 9, 2014. 9 pages.
Database PubChem Compound. Compound Summary for: CID 3243396. http://pubchem.ncbi.nlm.nih.gov/summary/summary.cgi?cid=3243396. XP002729649. Published Aug. 16, 2005. Printed Nov. 9, 2014. 10 pages.
Database PubChem Compound. Compound Summary for: CID 9550635. http://pubchem.ncbi.nlm.nih.gov/summary/summary,cgi?cid=9550635. XP002729650. Published Oct. 20, 2006. Printed Nov. 9, 2014. 9 pages.
Database PubChem Compound. Compound Summary for: CID 9550628. http://pubchem.ncbi.nlm.nih.gov/summary/summary,cgi?cid=9550628. XP002729651. Published Oct. 20, 2006. Printed Nov. 9, 2014. 9 pages.
Database PubChem Compound. Compound Summary for: CID 3244433 http://pubchem.ncbi.nlm.nih.gov/summary/summary,cgi?cid=3244423. XP002729654. Published Aug. 16, 2005. Printed Nov. 9, 2014. 9 pages.

(Continued)

*Primary Examiner* — Samantha Shterengarts
(74) *Attorney, Agent, or Firm* — Shawn D. Britt

(57) ABSTRACT

The present invention provides a compound of formula (I) or a pharmaceutically acceptable salt thereof;

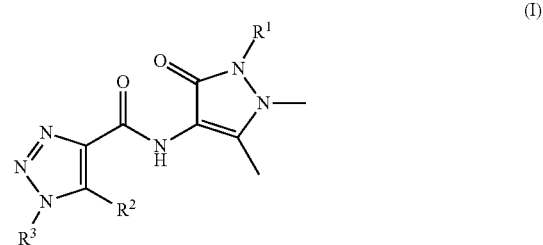

(I)

a method for manufacturing the compounds of the invention, and its therapeutic uses. The present invention further provides a combination of pharmacologically active agents and a pharmaceutical composition.

11 Claims, No Drawings

(56) References Cited

OTHER PUBLICATIONS

Database PubChem Compound. Compound Summary for: CID 1302330. http://pubchem.ncbi.nlm.nih.gov/summary/summary,cgi?cid=1302330. XP002729652. Published Jul. 11, 2005. Printed Nov. 9, 2014. 11 pages.
Database PubChem Compound. Compound Summary for: CID 9550632. http://pubchem.ncbi.nlm.nih.gov/summary/summary,cgi?cid=9550632. XP002729653. Published Oct. 20, 2006. Printed Nov. 9, 2014. 10 pages.
Database PubChem Compound. Compound Summary for: CID 9550738. http://pubchem.ncbi.nlm.nih.gov/summary/summary,cgi?cid=9550738. XP002729655. Published Oct. 20, 2006. Printed Nov. 9, 2014. 9 pages.
Database PubChem Compound. Compound Summary for: CID 3242075. http://pubchem.ncbi.nlm.nih.gov/summary/summary,cgi?cid=3242075. XP002729656. Published Aug. 16, 2005. Printed Nov. 9, 2014. 10 pages.
Database PubChem Compound. Compound Summary for: CID 9551038. http://pubchem.ncbi.nlm.nih.gov/summary/summary,cgi?cid=9551038. XP002729657. Published Oct. 20, 2006. Printed Nov. 9, 2014. 10 pages.
Database PubChem Compound. Compound Summary for: CID 3242216. http://pubchem.ncbi.nlm.nih.gov/summary/summary,cgi?cid=3242216. XP002729658 Published Aug. 16, 2005. Printed Nov. 9, 2014. 10 pages.
CAS Registry No. 898468-25-2. "3-Isoxazolecarboxamide, N-(2,3-dihydro-1,5-dimethyl-3-oxo-2-phenyl-1H-pyrazol-4-yl)-5-(4-ethoxyphenyl)—(CA Index Name)." Aug. 3, 2006.
CAS Registry No. 1015557-03-5. "3-Isoxazolecarboxamide, N-(2,3-dihydro-1,5-dimethyl-3-oxo-2-phenyl-1H-pyrazol-4-yl)-5-[4-(ethylsulfonyl)phenyl]—(CA Index Name)." Apr. 18, 2008.
CAS Registry No. 912760-79-3. "3-Isoxazolecarboxamide, 5-(3-chlorophenyl)-N-(2,3-dihydro-1,5-dimethyl-3-oxo-2-phenyl-1H-pyrazol-4-yl)—(CA Index Name)." Nov. 9, 2006.
CAS Registry No. 912781-64-7. "3-Isoxazolecarboxamide, N-(2,3-dihydro-1,5-dimethyl-3-oxo-2-phenyl-1H-pyrazol-4-yl)-5-(2-hydroxyphenyl)—(CA Index Name)." Nov. 9, 2006.
CAS Registry No. 912788-96-6. "3-Isoxazolecarboxamide, N-(2,3-dihydro-1,5-dimethyl-3-oxo-2-phenyl-1H-pyrazol-4-yl)-5-(4-hydroxyphenyl)—(CA Index Name)." Nov. 9, 2006.
CAS Registry No. 912791-65-2. "3-Isoxazolecarboxamide, 5-(4-bromophenyl)-N-(2,3-dihydro-1,5-dimethyl-3-oxo-2-phenyl-1H-pyrazol-4-yl)—(CA Index Name)." Nov. 9, 2006.
CAS Registry No. 1209692-48-7. "3-Isoxazolecarboxamide, N-(2,3-dihydro-1,5-dimethyl-3-oxo-2-phenyl-1H-pyrazol-4-yl)-5-(3-pyridinyl)—(CA Index Name)." Mar 14, 2010.
CAS Registry No. 12797-84-3. "3-Isoxazolecarboxamide, N-(2,3-dihydro-1,5-dimethyl-3-oxo-2-phenyl-1H-pyrazol-4-yl)-5-(3,4-dimethoxyphenyl)—(CA Index Name)." Nov. 9, 2006.
CAS Registry No. 898498-23-2. "3-Isoxazolecarboxamide, N-(2,3-dihydro-1,5-dimethyl-3-oxo-2-phenyl-1H-pyrazol-4-yl)-5-(3,4-dimethylphenyl)—(CA Index Name)." Aug. 3, 2006.
CAS Registry No. 717878-93-8. "3-Isoxazolecarboxamide, N-(2,3-dihydro-1,5-dimethyl-3-oxo-2-phenyl-1H-pyrazol-4-yl)-5-(4-methylphenyl)—(CA Index Name)." Jul. 28, 2004.
CAS Registry No. 1015604-48-4. "3-Isoxazolecarboxamide, N-(2,3-dihydro-1,5-dimethyl-3-oxo-2-phenyl-1H-pyrazol-4-yl)-5-[4-(propylsulfonyl)phenyl]—(CA Index Name)." Apr. 18, 2008.
CAS Registry No. 912775-67-8. "3-Isoxazolecarboxamide, 5-(3,4-dichlorophenyl)-N-(2,3-dihydro-1,5-dimethyl-3-oxo-2-phenyl-1H-pyrazol-4-yl)—(CA Index Name)." Nov. 9, 2006.
CAS Registry No. 912787-86-1. "3-Isoxazolecarboxamide, 5-(4-chlorophenyl)-N-(2,3-dihydro-1,5-dimethyl-3-oxo-2-phenyl-IH-pyrazol-4-yl)—(CA Index Name)." Nov. 9, 2006.
CAS Registry No. 912790-12-6. "3-Isoxazolecarboxamide, N-(2,3-dihydro-1 ,5-dimethyl-3-oxo-2-phenyl-1H-pyrazol-4-yl)-5-(3-hydroxyphenyl)—(CA Index Name)." Nov. 9, 2006.
CAS Registry No. 912795-89-2. "3-Isoxazolecarboxamide, N-(2,3-dihydro-1 ,5-dimethyl-3-oxo-2-phenyl-1H-pyrazol-4-yl)-5-(4-methoxyphenyl)—(CA Index Name)." Nov. 9, 2006.
CAS Registry No. 206037-29-7. "3-Isoxazolecarboxamide, 5-(3,4-difluorophenyl)-N-(2,3-dihydro-1,5-dimethyl-3-oxo-2-phenyl-1H-pyrazol-4-yl)—(CA Index Name)." Feb. 11, 2010.
CAS Registry No. 901665-66-5. "3-Isoxazolecarboxamide, 5-(2,3-dihydro-1,4-benzodioxin-6-yl)-N-(2,3-dihydro-1,5-dimethyl-3-oxo-2-phenyl-1H-pyrazol-4-yl)—(CA Index Name)" Aug. 16, 2006.
CAS Registry No. 907986-78-1. Index Name Not Yet Assigned. Sep. 20, 2006.
CAS Registry No. 1302184-45-7. "3-Isoxazolecarboxamide, N-(2,3-dihydro-1,5-dimethyl-3-oxo-2-phenyl-1H-pyrazol-4-yl)-5-(2-fluorophenyl)—(CA Index Name)." May 29, 2011.
CAS Registry No. 688050-41-1. "3-Isoxazolecarboxamide, N-(2,3-dihydro-1 ,5-dimethyl-3-oxo-2-phenyl-1H-pyrazol-4-yl)-5-(4-fluorophenyl)—(CA Index Name)." Jun. 1, 2004.
International Search Report and Written Opinion for International Application No. PCT/IB2015/001539 dated Oct. 27, 2015.
Database PubChem Compound. Compound Summary for: CID 55855650. XP002727692. Published on Jan. 25, 2012. Printed on Jul. 23, 2014. 3 pages. https://pubchem.ncbi.nlm.nih.gov/summary/summary.cgi?cid=55855650.
Database PubChem Compound. Compound Summary for: CID 55882610. XP002727693. Published on Jan. 25, 2012. Printed on Jul. 23, 2014. 3 pages. https://pubchem.ncbi.nlm.nih.gov/summary/summary.cgi?cid=55882610.

CARBOXAMIDE DERIVATIVES

This application is a Continuation of U.S. patent application Ser. No. 14/711,693 filed on May 13, 2015; which claims the benefit of priority to European Priority Application No. 14168319.3 filed on May 14, 2014; the contents of these applications are incorporated herein by reference.

FIELD OF THE INVENTION

The present invention describes organic compounds useful in therapy. The compounds demonstrate properties as selective Smurf-1 inhibitors and may thus be useful in the treatment of a range of disorders, particularly pulmonary arterial hypertension as well as other disorders such as glaucoma, hereditary hemorrhagic telangiectasia (HHT), proteinuria, wound healing, COPD and asthma.

BACKGROUND OF THE INVENTION

Smurf-1 (Smad ubiquitination regulatory factor 1) is a member of the HECT family of E3 ubiquitin ligase marking specific substrates for proteolytic degradation via the ubiquitin-dependent proteolytic pathway. Major substrates of Smurf-1 include RhoA, bone morphogenetic protein (BMP) receptor (BMPR) 1 and 2, smad1 and 5, TNFα receptor associated factor (TRAF) 6 and myD88 (Andrews, P. S. et al. Assay Drug Dev. Technol. 2010). Given the list of substrates, Smurf-1 has established roles in regulating BMP signaling (Chen, D et al. Growth Factors, 2004), neuronal cell polarity (Stiess, M. and Bradke, F. Neuron, 2011), cell migration (Huang, C. Cell Adh. Migr. 2010), tumor cell invasion (Sahai, E. et al. JCB, 2007), mitochondrial autophagy (Orvedahl, A. Nature, 2011) mesenchymal stem cell proliferation (Zhao, L. et al. J. Bone Miner. Res. 2010) and epithelial-mesenchymal transition (EMT) (Ozdamar, B et al. Science 2005).

Pulmonary arterial hypertension (PAH) is a life-threatening aggressive and complex disease of multiple etiologies, characterized by a progressive pulmonary vasculopathy leading to right ventricular hypertrophy/failure and in most cases premature death. Current pharmacological therapies are palliative. Whilst improvements in life expectancy have been observed, current therapies, which focus on altering the vasoconstrictive elements of the disease, do not halt or reverse progression of the disease, and transplantation (double lung or heart-lung) remains the only curative treatment. Given the limited effect of current treatment classes, novel therapies targeting the underlying progressive pulmonary vascular remodeling of PAH are needed.

Germline mutations in the transforming growth factor β (TGF-β) superfamily receptor bone morphogenetic protein receptor II (BMPR-II) gene are prevalent in seventy percent of heritable and some sporadic forms of idiopathic PAH (IPAH). Bone morphogenetic proteins are signaling molecules that belong to the TGF-β superfamily. Bone morphogenetic proteins were originally identified by their ability to induce formation of cartilage and bone, and subsequently identified to be multifunctional proteins that regulate a wide spectrum of function such as proliferation, differentiation, and apoptosis in a large variety of cell types, including osteoblasts, epithelial cells, neurons, immune cells, and smooth muscle cells. So far, >20 mammalian BMPs have been identified, but only three type I and three type II receptors (BMPR-I and BMPR-II, respectively) that are capable of binding with BMPs have been cloned in mammals. Bone morphogenetic proteins are synthesized and secreted from a variety of cell types, including pulmonary vascular smooth muscle cells and endothelial cells. In addition to mutations in BMPR-I and -II, lungs from patients with non-familial PAH display markedly reduced levels of vascular BMPR-1 and -II implying a central role for disrupted BMP signaling in many forms of PAH (Du, L et al. N. Eng. J. Med, 2003). Restoration of BMP signaling in the pulmonary vasculature of PAH patients is therefore of considerable interest in the development of novel anti-remodeling therapeutics for the treatment of PAH.

Smurf-1 has been shown to mediate degradation of BMPR-I, -II and smad1 and 5 in a variety of cell types including osteoblasts (Zhao, M et al. JBC, 2003), myoblasts (Ying, S X et al. JBC, 2003), lung epithelium (Shi W, et al. Am. J. Physiol. Cell. Mol. Physiol, 2004), neuronal tissue (Kallan, T et al. Mol. Cell. Biol, 2009) and endocardial cells (Towsend, T A, et al. Cells Tissues Organs, 2011). Recently, the first evidence has emerged supporting a role for Smurf-1 in PAH where enhanced levels of Smurf-1 were observed in the chronic hypoxia and monocrotaline pre-clinical in-vivo models of PAH and associated with down-regulation of BMPR1 and 2 (Murakami, K, et al. Exp. Biol. Med, 2010 and Yang, J. et al. Circ. Res, 2010).

SUMMARY OF THE INVENTION

There remains a need for new treatments and therapies for pulmonary arterial hypertension as well as other disorders such as glaucoma, hereditary hemorrhagic telangiectasia (HHT), proteinuria, wound healing, COPD and asthma. The invention provides compounds, pharmaceutically acceptable salts or co-crystals thereof, pharmaceutical compositions thereof and combinations thereof, which compounds are Smurf-1 inhibitors. The invention further provides methods of treating, preventing, or ameliorating pulmonary arterial hypertension, comprising administering to a subject in need thereof an effective amount of a Smurf-1 inhibitor.

According to a first aspect of the invention, Embodiment 1, there is provided a compound of formula (I):

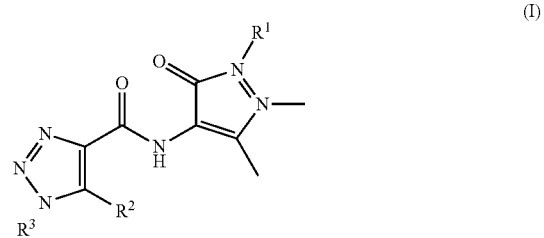

or a pharmaceutically acceptable salt or co-crystal thereof, wherein
$R^1$ is $(C_3-C_6)$alkyl or $(C_3-C_6)$cycloalkyl;
$R^2$ is methyl;

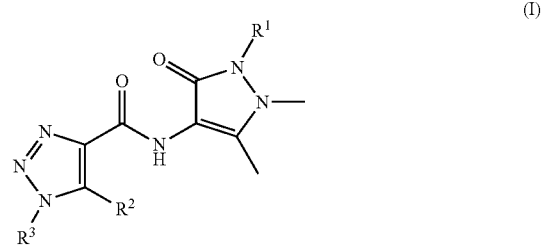

$R^3$ is

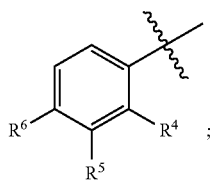

$R^4$ and $R^5$ are independently selected from hydrogen, halo, $(C_3-C_6)$cycloalkyl, $(C_1-C_4)$alkyl, halo$(C_1-C_4)$alkyl, $(C_1-C_4)$alkoxy, halo$(C_1-C_4)$alkoxy or —$(C_1-C_2)$alkyl$(C_1-C_2)$alkoxy; or $R^2$ and $R^4$ may be taken together with the carbon atoms to which they are attached to form an azepine ring and $R^5$ is H;

$R^6$ is halo, $(C_3-C_6)$cycloalkyl, $(C_1-C_4)$alkyl, halo$(C_1-C_4)$alkyl, $(C_1-C_4)$alkoxy, halo$(C_1-C_4)$alkoxy or —$(C_1-C_2)$alkyl$(C_1-C_2)$alkoxy;

OR $R^1$ is 2-fluorophenyl;
$R^2$ is methyl; and
$R^3$ is phenyl, substituted with one or two substituents independently selected from chloro and cyclopropyl.

In another embodiment of the invention is provided a compound of Formula (I) as defined above or a pharmaceutically acceptable salt thereof.

In another embodiment, the invention provides a pharmaceutical composition comprising a therapeutically effective amount of a compound according to the definition of formula (I), or a pharmaceutically acceptable salt or co-crystal thereof, or subformulae thereof and one or more pharmaceutically acceptable carriers.

In another embodiment the pharmaceutical composition comprises a compound of formula (I) or a pharmaceutically acceptable salt thereof and one or more pharmaceutically acceptable carriers.

In another embodiment, the invention provides a method of treating a disorder or disease selected from Pulmonary Hypertension, including Pulmonary arterial hypertension (PAH), Fibrosis, Rheumatoid Arthritis, and Fracture healing comprising administering to the subject a therapeutically effective amount of the compound according to the definition of formula (I), or a salt thereof, or subformulae thereof or a pharmaceutically acceptable salt or co-crystal.

In another embodiment, the invention provides a method of treating a disorder or disease selected from glaucoma, hereditary hemorrhagic telangiectasia (HHT), proteinuria, wound healing, as well as COPD and asthma, comprising administering a therapeutically effective amount of a compound of formula (I), or a pharmaceutically acceptable salt thereof, to subject in recognized need thereof.

In another embodiment, the invention provides a combination, in particular a pharmaceutical combination, comprising a therapeutically effective amount of the compound according to the definition of formula (I), or a pharmaceutically acceptable salt or co-crystal thereof, or subformulae thereof and one or more therapeutically active agents.

In another embodiment the invention provides a combination, in particular a pharmaceutical combination, comprising a therapeutically effective amount of a compound of formula (I), or a pharmaceutically acceptable salt thereof and one or more therapeutically active agents.

Various embodiments of the invention are described herein.

DETAILED DESCRIPTION

The invention therefore provides a compound of the formula (I) or a pharmaceutically acceptable salt or co-crystal thereof, as described hereinabove as Embodiment 1.

Embodiment 2. A compound according to Embodiment 1 or a pharmaceutically acceptable salt or co-crystal thereof, wherein $R^1$ is iso-propyl, cyclobutyl or cyclohexyl.

Embodiment 3. A compound according to Embodiment 1 or Embodiment 2 or a pharmaceutically acceptable salt or co-crystal thereof, wherein $R^1$ is cyclohexyl.

Embodiment 4. A compound according to any preceding Embodiment or a pharmaceutically acceptable salt or co-crystal thereof, wherein
$R^3$ is

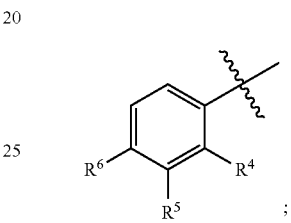

$R^4$ and $R^6$ are independently selected from chloro, fluoro, cyclopropyl, methyl, methoxy, trifluoromethoxy, trifluoromethyl; and $R^5$ is hydrogen.

Embodiment 5. A compound according to any preceding Embodiment, or a pharmaceutically acceptable salt or co-crystal thereof, wherein $R^3$ is

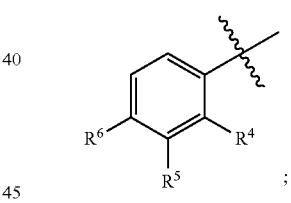

$R^4$ and $R^6$ are independently selected from chloro and cyclopropyl; and $R^5$ is hydrogen.

Embodiment 6. A compound of formula (I) according to Embodiment 1, wherein the compound is selected from Example 1:
1-(2-Chloro-4-methoxyphenyl)-N-(2-cyclohexyl-1,5-dimethyl-3-oxo-2,3-dihydro-1H-pyrazol-4-yl)-5-methyl-1H-1,2,3-triazole-4-carboxamide Example 2:
N-(2-Cyclohexyl-1,5-dimethyl-3-oxo-2,3-dihydro-1H-pyrazol-4-yl)-1-(2,4-dichlorophenyl)-5-methyl-1H-1,2,3-triazole-4-carboxamide Example 3:
N-(2-Cyclohexyl-1,5-dimethyl-3-oxo-2,3-dihydro-1H-pyrazol-4-yl)-1-(4-methoxy-2-(trifluoromethyl)phenyl)-5-methyl-1H-1,2,3-triazole-4-carboxamide Example 4:
N-(2-Cyclohexyl-1,5-dimethyl-3-oxo-2,3-dihydro-1H-pyrazol-4-yl)-1-(4-methoxy-3-methylphenyl)-5-methyl-1H-1,2,3-triazole-4-carboxamide Example 5:
1-(2-Chloro-4-(trifluoromethoxy)phenyl)-N-(2-cyclohexyl-1,5-dimethyl-3-oxo-2,3-dihydro-1H-pyrazol-4-yl)-5-methyl-1H-1,2,3-triazole-4-carboxamide
Example 6:
1-(4-Chlorophenyl)-N-(2-cyclohexyl-1,5-dimethyl-3-oxo-2,3-dihydro-1H-pyrazol-4-yl)-5-methyl-1H-1,2,3-triazole-4-carboxamide
Example 7:
1-(2,4-Dichlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide
Example 8:
1-(4-Chlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide
Example 9:
1-(2-Chloro-4-(trifluoromethoxy)phenyl)-N-(2-(2-fluorophenyl)-1,5-dimethyl-3-oxo-2,3-dihydro-1H-pyrazol-4-yl)-5-methyl-1H-1,2,3-triazole-4-carboxamide
Example 10:
1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide
Example 11:
1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide
Example 12:
1-(2-Chloro-4-cyclopropylphenyl)-N-(2-cyclohexyl-1-methyl-$d_3$,5-methyl-3-oxo-2,3-dihydro-1H-pyrazol-4-yl)-5-methyl-1H-1,2,3-triazole-4-carboxamide
Example 13:
1-(4-Chloro-2-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide
Example 14:
1-(4-Chloro-2-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide
Example 15:
N-(2-Cyclohexyl-1,5-dimethyl-3-oxo-2,3-dihydro-1H-pyrazol-4-yl)-1-(2-cyclopropyl-4-fluorophenyl)-5-methyl-1H-1,2,3-triazole-4-carboxamide
Example 16:
N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide
Example 17:
N-(2-Cyclohexyl-1,5-dimethyl-3-oxo-2,3-dihydro-1H-pyrazol-4-yl)-1-(4-methoxyphenyl)-5-methyl-1H-1,2,3-triazole-4-carboxamide.
Embodiment 7. A compound of formula (I), or a pharmaceutically acceptable salt thereof, according to embodiment 1, wherein the compound is selected from
Example 10:
1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide
Example 11:
1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide
Example 12:
1-(2-Chloro-4-cyclopropylphenyl)-N-(2-cyclohexyl-1-methyl-$d_3$,5-methyl-3-oxo-2,3-dihydro-1H-pyrazol-4-yl)-5-methyl-1H-1,2,3-triazole-4-carboxamide and
Example 16:
N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide;
or a pharmaceutically acceptable salt or co-crystal thereof.

As used herein, the term "halo" (or halogen) refers to fluorine, bromine, chlorine or iodine, in particular fluorine, chlorine. Halogen-substituted groups and moieties, such as alkyl substituted by halogen (haloalkyl) can be mono-, poly- or per-halogenated.

As used herein, the term "alkyl" refers to a fully saturated branched or unbranched hydrocarbon moiety having up to 10 carbon atoms. Unless otherwise provided, alkyl refers to hydrocarbon moieties having 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Representative examples of branched alkyl include, but are not limited to, iso-propyl, sec-butyl, iso-butyl, tert-butyl, isopentyl, 3-methylhexyl, 2,2-dimethylpentyl, 2,3-dimethylpentyl, and the like. A substituted alkyl is an alkyl group containing one or more, such as one, two or three substituents selected from halogen, hydroxy or alkoxy groups.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 1-4 carbon atoms.

As used herein, the term "haloalkoxy" refers to an alkoxy as defined herein, which is substituted by one or more halo groups as defined herein.

As used herein, the term "cycloalkyl" refers to saturated monocyclic, bicyclic, or spirocyclic hydrocarbon groups of 3-8 carbon atoms. Unless otherwise provided, cycloalkyl refers to cyclic hydrocarbon groups having between 3 and 6 ring carbon atoms.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

In many cases, the compounds of the present invention are capable of forming acid and/or base salts by virtue of the carboxamide group or groups similar thereto.

Pharmaceutically acceptable acid addition salts or co-crystals can be formed with inorganic acids and organic acids.

Inorganic acids from which salts or co-crystals can be derived include, for example, hydrochloric acid, hydrobromic acid, sulfuric acid, nitric acid, phosphoric acid, and the like.

Organic acids from which salts or co-crystals can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, and the like.

Pharmaceutically acceptable base addition salts or co-crystals can be formed with inorganic and organic bases.

Inorganic bases from which salts or co-crystals can be derived include, for example, ammonium salts and metals from columns I to XII of the periodic table. In certain embodiments, the salts are derived from sodium, potassium, ammonium, calcium, magnesium, silver and zinc; particularly suitable salts include ammonium, potassium, sodium, calcium and magnesium salts.

Organic bases from which salts or co-crystals can be derived include, for example, primary, secondary, and tertiary amines, substituted amines including naturally occurring substituted amines, cyclic amines, basic ion exchange resins, and the like. Certain organic amines include cholinate, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polyga- lacturonate, propionate, sebacate, stearate, succinate, sulfate, tartrate, tosylate trifenatate, or xinafoate salt or co-crystal form.

In one embodiment, the present invention provides 1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another embodiment, the present invention provides 1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another embodiment, the present invention provides 1-(2-Chloro-4-cyclopropylphenyl)-N-(2-cyclohexyl-1-methyl-$d_3$,5-methyl-3-oxo-2,3-dihydro-1H-pyrazol-4-yl)-5-methyl-1H-1,2,3-triazole-4-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another embodiment, the present invention provides N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another aspect, the present invention provides compounds of formula I in sodium, potassium, ammonium, calcium, magnesium, silver, zinc, cholinate, lysine, meglumine, piperazine or tromethamine salt or co-crystal form.

In one embodiment, the present invention provides 1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide in sodium, potassium, ammonium, calcium, magnesium, silver, zinc, cholinate, lysine, meglumine, piperazine or tromethamine salt or co-crystal form.

In another embodiment, the present invention provides 1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide in sodium, potassium, ammonium, calcium, magnesium, silver, zinc, cholinate, lysine, meglumine, piperazine or tromethamine salt or co-crystal form.

In another embodiment, the present invention provides 1-(2-Chloro-4-cyclopropylphenyl)-N-(2-cyclohexyl-1-methyl-d$_3$,5-methyl-3-oxo-2,3-dihydro-1H-pyrazol-4-yl)-5-methyl-1H-1,2,3-triazole-4-carboxamide in sodium, potassium, ammonium, calcium, magnesium, silver, zinc, cholinate, lysine, meglumine, piperazine or tromethamine salt or co-crystal form.

In another embodiment, the present invention provides N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide in sodium, potassium, ammonium, calcium, magnesium, silver, zinc, cholinate, lysine, meglumine, piperazine or tromethamine salt or co-crystal form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Embodiment 8 provides a compound of formula (I), or a pharmaceutically acceptable salt or co-crystal, wherein when R$^3$ is

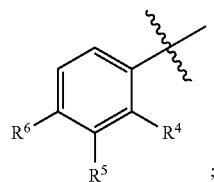

;

R$^4$ and R$^6$ are independently selected from chloro, fluoro, cyclopropyl, methyl, methoxy, trifluoromethoxy, trifluoromethyl; the methyl and methoxy groups may be deuterated.

Pharmaceutically acceptable solvates in accordance with the invention include those wherein the solvent of crystallization may be isotopically substituted, e.g. D$_2$O, d$_6$-acetone, d$_6$-DMSO.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Smurf-1, or (ii) associated with Smurf-1 activity, or (iii) characterized by activity (normal or abnormal) of Smurf-1; or (2) reduce or inhibit the activity of Smurf-1; or (3) reduce or inhibit the expression of Smurf-1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Smurf-1; or at least partially reducing or inhibiting the expression of Smurf-1.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80 enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Generic Schemes

The compounds of the present invention may be prepared by the routes described in the following Schemes or the Examples.

All abbreviations are as defined in the examples section hereinbelow.

Scheme 1

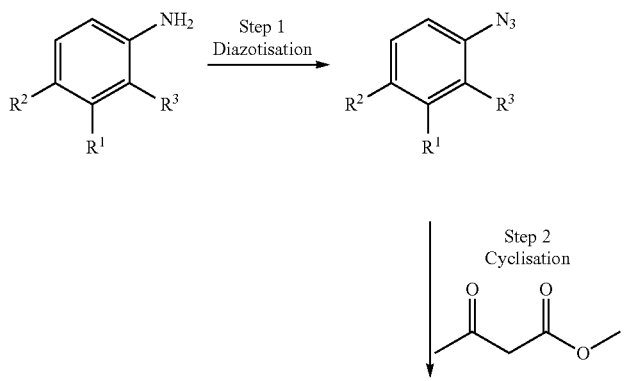

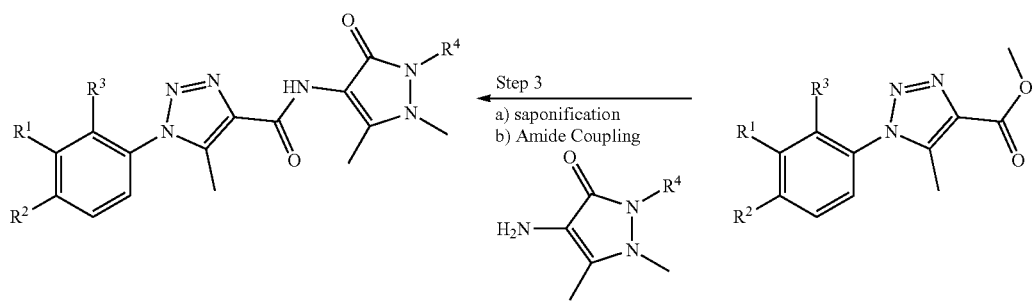

Step 1: Diazotisation

Typical conditions: a) Sodium nitrite at 0-5° C., in a suitable solvent with the addition of a nucleophillic azide source Preferred conditions: Sodium nitrite in Acetic acid at 0° C. in the prescence of sodium azide.

Step 2: Cyclisation

Typical conditions: A betoketo ester and a strong base in a polar solvent at 50-80° C. Preferred conditions: Methyl 3 oxobutanoate, with sodium methoxide in methanol at 60° C.

Step 3a Saponification

Typical conditions: A suitable aqueous base, optionally with a suitable co-solvent such as THF Preferred conditions: 2M Sodium Hydroxide (aq.) with THF at r.t. for 30 mins Step 3b Amide Coupling Typical conditions: A suitable coupling reagent such as Oxalyl chloride, HATU, T3P, EDCI etc, in the presence of a suitable base such as triethylamine, DIPEA etc, in a suitable aprotic solvent.

Preferred conditions: Oxalyl chloride, DMF(cat), DCM, triethylamine

Scheme 2

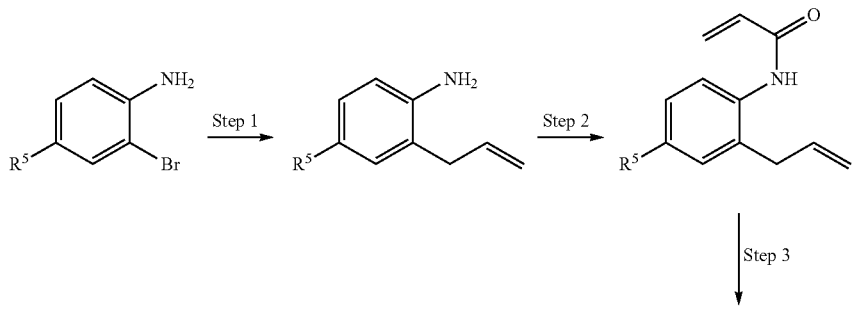

-continued

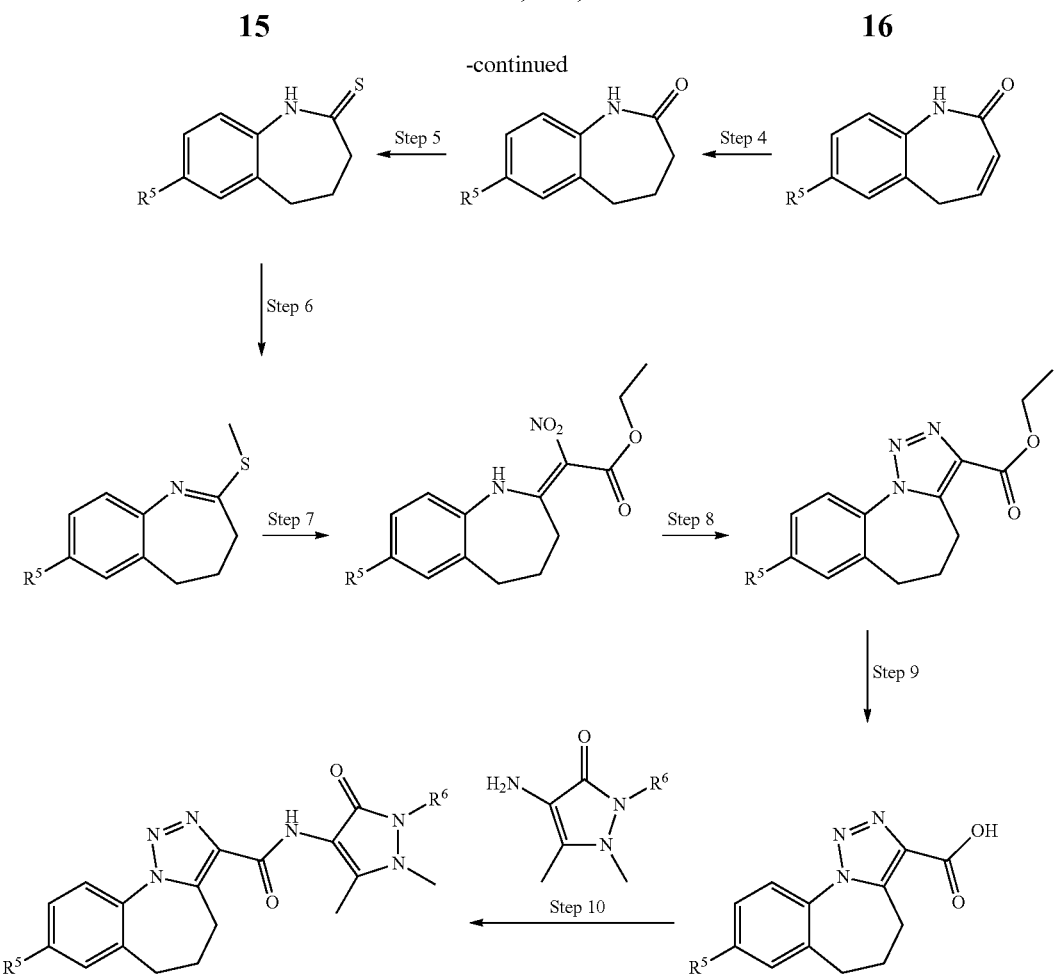

Step 1: A Palladium Catalysed Allylation Cross Coupling Reaction.

Typical conditions: Palladium (0) catalyst; an allyl stannane; in a suitable solvent; at 80-110° C. Preferred conditions: tetrakistriphenylphosphine palladium(0), allyl tributyltin in DMF at 80° C.

Step 2: Amide Coupling

Typical conditions: A suitable acid chloride such as acryloyl chloride in the presence of a suitable base such as triethylamine, in a suitable aprotic solvent.

Preferred conditions: acryloyl chloride, triethylamine in tetrahydrofuran at −10° C.

Step 3: Ring Closing Metathesis

Typical conditions: A suitable catalyst, in a suitable solvent.

Preferred conditions: 5% {[2-(i-propoxy)-5-(N,N-dimethylaminosulfonyl)phenyl]methylene}(tricyclohexylphosphine) ruthenium(II) dichloride in DCM.

Step 4 Hydrogenation

Typical conditions: A non-soluble Palladium catalyst, Hydrogen gas, in a suitable solvent such as an alcohol Preferred conditions: 10% Palladium on Carbon and Hydrogen gas in ethanol.

Step 5 Thioamide Formation

Typical conditions: A suitable source of sulfur in a suitable solvent with heating Preferred conditions: Lawesson's Reagent in toluene at 110° C.

Step 6 Methylation

Typical conditions: Methyl halide in the presence of a suitable base in a suitable solvent Preferred conditions: Methyl Iodide in the presence of potassium hydroxide in acetone.

Step 7 Condensation Reaction

Typical conditions: An alpha nitroester in the prescence of a non-nucleophilic base with heating Preferred conditions: Ethyl nitroacetate and DBU at 40° C.

Step 8 Reductive Triazole Formation

Preferred conditions: Zinc and isoamyl nitrie in acetic acid and triclhoroacetic acid.

Step 9 Saponification

Typical conditions: A suitable aqueous base, optionally with a suitable co-solvent such as THF Preferred conditions: 2M Sodium Hydroxide (aq.) with THF and methanol at r.t. for 30 mins.

Step 10 Amide Coupling

Typical conditions: A suitable coupling reagent such as Oxalyl chloride, HATU, T3P, EDCI etc, in the presence of a suitable base such as triethylamine, DIPEA etc, in a suitable aprotic solvent.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable pharmaceutically acceptable salt or co-crystal, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations.

Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in pharmaceutically acceptable salt form, exhibit valuable pharmacological properties, e.g. Smurf-1 modulating properties, e.g. as indicated in vitro and in vivo tests as provided in the next sections, and are therefore indicated for therapy or for use as research chemicals, e.g. as tool compounds.

Compounds of the invention are useful in the treatment of indications including:
Pulmonary Hypertension, including Pulmonary arterial hypertension (PAH)
Fibrosis
Rheumatoid Arthritis
Fracture healing
Glaucoma
hereditary hemorrhagic telangiectasia (HHT)
proteinuria
wound healing
COPD
asthma
Pulmonary Arterial Hypertension (PAH)

Pulmonary arterial hypertension has a multifactorial pathobiology. Vasoconstriction, remodeling of the pulmonary vessel wall and thrombosis contribute to increased pulmonary vascular resistance in PAH (Humbert et al, J. Am. Coll. Cardiol., 2004.). The compounds of the present invention disclosed herein are useful in the treatment of PAH and symptoms thereof. Pulmonary arterial hypertension shall be understood to encompass the following forms of pulmonary hypertension: idiopathic PAH (IPAH); heritable PAH (HPAH); PAH induced by drugs or toxins, PAH associated with other conditions (APAH), such as PAH associated with connective tissue diseases, PAH associated with HIV infection, PAH associated with portal hypertension, PAH associated with congenital heart diseases, PAH associated with schistosomiasis, PAH associated chronic haemolytic anaemia, or peristent pulmonary hypertension of the newborn (Gallè et al, ERJ, 2009; Simonneau et al, JACC, 2009).

Idiopathic PAH refers to PAH of undetermined cause. Heritable PAH refers to PAH for which hereditary transmission is suspected or documented including those harboring mutations in the BMP receptor, BMPR2 or those with mutations in ALK1 or endoglin (with or without hereditary hemorrhagic talangiectasia).

PAH associated with drugs or toxins shall be understood to encompass PAH associated with ingestion of aminorex, a fenfluramine compound (e.g. fenfluramine or dexfenfluramine), certain toxic oils (e.g. rapeseed oil), pyrrolizidine alkaloids (e.g. bush tea), monocrotaline, amphetamines, L-tryptophan, methamphetamines, cocaine, phenylpropanolamine, St John's Wort, chemotherapeutic agents or SSRI's.

PAH associated with connective tissue diseases shall be understood to encompass PAH associated with systemic sclerosis, lung fibrosis, polymyositis, rheumatoid arthritis, Sjogren syndrome or PAH associated with systemic lupus erythematosis.

PAH associated with congenital heart diseases shall be understood to encompass patients with systemic to pulmonary shunts, PAH associated with Eisenmenger syndrome, small ventricular-septal or atrial-septal defects or PAH associated with corrective cardiac surgery.

PAH associated with chronic hemolytic anemia shall be understood to encompass patients with chronic hereditary and acquired anemias including patients with sickle cell disease, thalassemia, hereditary spherocytosis, stomatocytosis and microangiopathic hemolytic anemia.

Symptoms of PAH include dyspnea, angina, syncope and edema (McLaughlin et al., Circulation, 2006, 114:1417-1431). The compounds of the present invention disclosed herein are useful in the treatment of symptoms of PAH.
Pulmonary Hypertension (PH)

Pulmonary hypertension (PH) shall be understood to be associated with the following conditions grouped according to the Dana Point clinical classification (Simonneau, G et al. JACCC, 2009):

Group 1'—PH shall be understood to be associated with patients harboring pulmonary veno-occlusive disease (PVOD) and pulmonary capillary hemangiomatosis (PCH).

Group 2—PH associated with left heart disease include those patients with left-sided ventricular or valvular diseases.

Group 3—PH as a result of lung diseases and/or hypoxia. Lung diseases resulting in PH shall be understood to encompass patients with pulmonary fibrosis, emphysema, combined pulmonary fibrosis and emphysema, bronchiectasis, cystic fibrosis and chronic obstructive lung disease (COPD).

Group 4—PH associated with chronic thromboembolism (CTEPH).

Group 5—PH associated with unclear or multifactoral etiologies. This category of PH patients shall be understood to encompass patients in one of the following groups: 1) chronic myeloproliferative disorders including polycythemia vera, essential thrombocythemia or chronic myeloid leukemia; 2) Systemic disorders including sarcoidosis, conditions resulting in destruction of the pulmonary capillary bed such as fibrosis, extrinsic compression of large pulmonary arteries, patients with Pulmonary Langerhan's cell histocytosis, lymphangioleiomyomatosis, neurofibromatosis type 1 and antineutrophil cytoplasmic antibodies-associated vasculitis; 3) Metabolic disorders including type Ia glycogen storage disease, deficiency of glucose-6-phosphatase, Gaucher disease and thyroid diseases (hypothyroidism and hyperthyroidism); 4) Encompassing patients with tumors that expand into the lumen of the pulmonary artery, occlusion of pulmonary microvasculature by metastatic tumor emboli, mediastinal fibrosis or patients with end-stage renal disease receiving long-term hemodialysis.
Fibrosis Dysregulation of the TGFβ/BMP signaling pathways have been shown to have a causative role in fibrosis of various organs including kidney, heart, lung, skin, pancreas and liver, as well as in systemic sclerosis and associated pathologies (as reviewed by Leask and Abraham, FASEB, 2004). It has been shown that BMP7 counteracts TGFβ1-induced epithelial-mesenchymal transition (EMT) (Zeisberg, M et al. Nat. Med, 2003) and collagen induction (Izumi, N et al. AJP. Lung, Cell, Mol., Physiol. 2005) both key mechanisms in the development of fibrosis. Direct evidence for a role of Smurf-1 in fibrotic pathologies was demonstrated in the unilateral ureteral obstruction (UUO) mouse model of progressive tubulointerstitial fibrosis of the kidney where enhanced levels of Smurf-1 were present in the diseased kidneys associated with decreased levels of the protective Smurf-1 substrate, Smad7 (Fukasawa, H et al. PNAS, 2004). More recently, a role for Smurf-1 in pulmonary fibrosis was suggested in data generated in pulmonary epithelial cells identifying a crucial role for the Smurf-1 substrate Smad7 in limiting EMT (Shukla, M A, et al. Am.

J. Resp. Cell. Mol. Biol. 2009). The compounds of the present invention disclosed herein are useful in the treatment of fibrosis and symptoms thereof. Fibrosis shall be understood to encompass the following: patients with pulmonary fibrosis, idiopathic pulmonary fibrosis, cystic fibrosis, cirrhosis, endomyocardial fibrosis, mediastinal fibrosis, myelofibrosis, retroperitoneal fibrosis, progressive massive fibrosis, nephrogenic systemic fibrosis, Crohn's Disease, keloid, old myocardial infarction, scleroderma (systemic sclerosis), arthrofibrosis or adhesive capsulitis.

Rheumatoid Arthritis

Pro-inflammatory cytokines such as tumor necrosis factor alpha (TNFα) play a key role in the onset and maintenance of chronic inflammatory conditions such as rheumatoid arthritis (RA). A reduction in bone density is commonly associated with RA and Smurf-1 has been shown to play a key role in mediating RA-induced bone loss. It was shown that TNFα triggered proteolytic degradation of the Smurf-1 substrates Smad1 and Runx2 both of which are essential for bone-forming osteoblast activity. Direct evidence in support of this link was demonstrated in smurf-1 KO mice where TNFα failed to impact osteoclast activity in bones from Smurf-1 KO mice but not those of corresponding wild-type mice (Guo, R et al. JBC, 2008). The compounds of the present invention disclosed herein are useful in the treatment of rheumatoid arthritis and symptoms thereof. RA shall be understood to encompass patients with chronic inflammation of the synovium secondary to swelling of synovial cells, excess synovial fluid and formation of fibrous tissue within joints. In addition, RA shall also encompass patients with RA due to a necrotizing granuloma, vasculitis, pyoderma gangrenosum, Sweet's syndrome, erythema nodosum, lobular panniculitis, atrophy of digital skin, palmar erythema or diffuse thinning of the skin. RA also extends to other organs and herein will encompass patients with fibrosis of the lungs, renal amyloidosis, atherosclerosis as a result of RA, pericarditis, endocarditis, left ventricular failure, valvulitis and fibrosis. RA will also encompass patients with ocular conditions of episcleritis and keratoconjunctivitis sicca, hematological disorders of warm autoimmune hemolytic anemia, neutropenia and thrmobocytosis, neurological conditions of peripheral neuropathy, mononeuritis multiplex and carpal tunnel syndrome, osteoporosis and lymphoma.

Fracture Healing

The BMP pathway plays a role here and Smurf-1 inhibitors increase BMP signaling. The compounds of the present invention disclosed herein are useful in the treatment of fracture healing and osseointegrationof implants and symptoms thereof. Fracture healing shall be understood to encompass the technique of bone fracture repair whereby an endosteal impant containing pores into which osteoblasts and supporting connective tissue can migrate is surgically implanted at the site of bone fracture. The administration of inhibitors of Smurf-1 following insertion of the above described implant may aid integration of the implant and expedite recovery by enhancing proliferation of mesenchymal stem cells which differentate into osteoblasts (Zhao, M et al. JBC, 2004).

Glaucoma

Elevated intraocular pressure (1OP) is one of the major risk factor for primary open angle glaucoma (POAG). 1OP is maintained in anterior chamber by aqueous humor produced in ciliary body and outflowed through trabecular meshwork region. Increase aqueous humor outflow resistance associated with accumulation of extracellular matrix (ECM) deposition in trabecular meshwork region has been observed in glaucoma patients. This ECM pathology in POAG patients resembles fibrosis induced by TGFb proteins in many non-ocular systems. TGFb2 induced IOP increase was demonstrated in pre-clinical in vivo and ex vivo models. In several small scale clinical studies, the level of TGFb2 protein in aqueous humor has also been reported to be elevated in POAG patients. Modulating the TGFb activity in glaucoma patients could potentially lower IOP and lead to novel glaucoma therapies (Wordinger R J JOURNAL OF OCULAR PHARMACOLOGY AND THERAPEUTICS Volume 30, Number 2, 2014). In view of the role of Smurf1 in the regulation of TGFb signaling through its substrates BMP9 and SMAD 7 the compounds of the present invention (or their pharmaceutically acceptable salts) described herein would be useful in the treatment of glaucoma.

Hereditary Hemorrhagic Telangiectasia (HHT)

Hereditary Hemorrhagic Telangiectasia (HHT), also known as Osler-Weber-Rendu Syndrome, is a genetic disorder of the blood vessels affecting from 1:5000 to 1:40,000. A person with HHT has a tendency to form blood vessels that lack normal capillaries between an artery and vein, causing arterial blood under high pressure to flow directly into a vein, which may rupture and bleed. Symptoms of HHT may manifest as mild to severe, with 90-95% of patients experiencing nosebleeds by adulthood, 90-95% developing telangiectasias on the face or hands by middle age, and 40% developing lung arteriovenous malformations (AVM), which can pose significant risk. AVMs may also occur in the brain, liver, and intestine, with varying severity of health implications. HHT can be treated, most often with coagulation therapy, embolization, or surgical removal of affected tissue. HHT mutations cause haploinsufficiency in BMP signaling (Ricard et al. Blood, 2010) resulting in a vessel maturation defect and excessive branching of the vasculature which is in part, attributed to impaired BMP9 signaling (Choi, et al. PlosOne, 2013). Smurf1 down-regulates BMP signaling (Murakami Exp. Biol. Res. 2010 and Cao, et al. Sci. Rep. 2014) and has been reported to be expressed in the endothelial cells (Crose, et al. JBC, 2009 and Human Protein Atlas and GeneCards) and therefore, Smurf1 inhibitors may serve to restore BMP signaling and correct the angiogenesis abnormality. As such the compounds of the present invention (or their pharmaceutically acceptable salts) described herein would be useful in the treatment of HHT.

Proteinuria

Abnormal amounts of protein in the urine are one of the earliest signs of chronic kidney disease which can result from hypertension, diabetes or diseases associated with inflammation in the kidneys. If left untreated, chronic kidney disease may progress to end-stage renal disease and kidney failure. Smurf1 is involved in multiple mechanisms associated with kidney function and proteinuria. The Smurf1 substrate Ras homolog gene family, member A (RhoA), plays a critical role in regulating the migration of kidney podocytes. Synaptopodin enables stress fiber formation within kidney podocytes by blocking the ability of Smurf1 to bind to and ubiquitinate RhoA thus promoting podocyte motility and modulation of sieving properties of the podocyte filtration barrier of the kidney (Asanuma, et al. Nat. Cell Biol. 2006). Additionally, the intracellular antagonist of transforming growth factor (TGF) β, Smad7 plays a key protective role in the kidney. Smurf1 activity has been shown to ubiquitinate and degrade Smad7 leading to tubulointerstitial fibrosis and kidney dysfunction (Fukasawa, et al. PNAS 2004). Together, these reports suggest that a Smurf1 inhibitor may enable podocyte migration and maintainance of the podocyte filtration barrier in addition to blocking propagation of pro-fibrotic signaling with the kidney ultimately providing therapeutic benefit for proteinuria. Accordingly the compounds of the invention (or their pharmaceutically acceptable salts) would be useful in the treatment of proteinuria.

Wound Healing

Chronic non-healing wounds are most common in people over the age of 60 resulting in a significant amount of physical pain and are broadly classified into three groups: venous ulcers, diabetic and pressure ulcers. The precise timing of activity of the transforming growth factor (TGF) β and bone morphogenic protein (BMP) signaling pathways is essential in normal wound healing regulating key pro-healing processes of fibroblast migration and extracellular matrix deposition, inflammatory cell influx, angiogenesis and re-epithelialization (Pakyari, M et al. Adv. Wound Care 2013). Prolonged activation of TGF β may result in delayed wound healing and therapeutic intervention of established non-healing wounds with anti-TGF β antibodies results in improved healing and reduced scar hypertrophy (Lu et al. J. Am. Coll. Surg. 2005). Smurf1 regulates the extent of TGF β and BMP signaling (Murakami Exp. Biol. Res. 2010 and Cao, et al. Sci. Rep. 2014, Wang et al. J. Cell. Mol. Med. 2012) and therefore, it is anticipated that a Smurf1 inhibitor would normalized excessive of TGF β signaling enabling healing of chronic wounds. Accordingly the compounds of the invention (or their pharmaceutically acceptable salts) would be useful in the treatment of chronic non-healing wounds and/or wound healing generally.

COPD and Asthma

Airway remodeling is evident in patients with chronic obstructive pulmonary disease (COPD) or asthma. The predominant features of airway remodeling in asthma are fibrosis, thickening of basement membrane, increased goblet cell numbers and enhanced smooth muscle cell mass with enhanced contractile response which are thought to be induced by chronic inflammation responsible for airway hyper-responsiveness and reversible airway obstruction (Carroll et al. Am. Rev Resp. Dis. 1993, Metcalfe, et al. Physiol. Rev. 1997 and Roche, et al. Lancet 1989). In COPD lung remodeling is characterized by disorganization of the epithelium in the large airways with squamous metaplasia, goblet cell hyperplasia and mucus hypersecretion, and small airway remodeling with expansion of smooth muscle, fibrosis and alveolar destruction in the development of emphysema ultimately resulting in restriction of airflow (De, Decramer, et al. Lancet, 2012, Pain et al. Eur. Respir. Rev. 2014 and Chung, Proc. Am. Thorac. Soc. 2005). In both diseases, there is evidence of down-regulated BMP signaling (Kariyawasam, et al. Am. J Resp. Crit. Care Med. 2008) and elevated TGF β (Mak. Et al. Respir. Med. 2009 and Chakir et al. J. All. Clin. Immunol. 2003) linked to pro-remodelling mechanism such as fibroblast-mesenchymal transition (Araya, et al. J. Clin. Invest. 2007), extracellular matrix deposition (Baarsma, et al. Am. J. Physiol. Lung Cell Mol. PHysiol. 2011) and inflammation (Chakir et al. J. All. Clin. Immunol. 2003). Smurf1 inhibitors may normalize TGF β signaling in critical pro-remodeling cells such as smooth muscle and fibroblasts and block progression of remodeling resulting in therapeutic benefit to COPD or asthma patients. Accordingly, the compounds of the invention (or their pharmaceutically acceptable salts) would be useful in the treatment of COPD and/or asthma.

Thus, as a further embodiment, the present invention provides the use of a compound of formula (I) or a pharmaceutically acceptable salt thereof in therapy. In a further embodiment, the therapy is selected from a disease which may be treated by inhibition of Smurf-1. In another embodiment, the disease is selected from the afore-mentioned list, suitably Pulmonary Hypertension, including Pulmonary arterial hypertension (PAH), Fibrosis, Rheumatoid Arthritis, and Fracture healing, more suitably Pulmonary arterial hypertension (PAH). In a yet further embodiment, the present invention provides the use of a compound of formula I or a pharmaceutically acceptable salt thereof, in the treatment of a disease selected from glaucoma, hereditary hemorrhagic telangiectasia (HHT), proteinuria, wound healing, COPD and asthma.

Thus, as a further embodiment, the present invention provides a compound of formula (I) or a pharmaceutically acceptable salt thereof for use in therapy. In a further embodiment, the therapy is selected from a disease which may be treated by inhibition of Smurf-1. In another embodiment, the disease is selected from the afore-mentioned list, suitably Pulmonary Hypertension, including Pulmonary arterial hypertension (PAH), Fibrosis, Rheumatoid Arthritis, and Fracture healing;

more suitably Pulmonary arterial hypertension (PAH). In a yet further embodiment, the present invention provides a compound of formula (I) or a pharmaceutically acceptable salt thereof for use in the treatment of a disease selected from glaucoma, hereditary hemorrhagic telangiectasia (HHT), proteinuria, wound healing, COPD and asthma.

In another embodiment, the invention provides a method of treating a disease which is treated by inhibition of Smurf-1 comprising the administration of a therapeutically acceptable amount of a compound of formula (I) or a pharmaceutically acceptable salt thereof. In a further embodiment, the disease is selected from the afore-mentioned list, suitably Pulmonary Hypertension, including Pulmonary arterial hypertension (PAH), Fibrosis, Rheumatoid Arthritis, and Fracture healing;

more suitably Pulmonary arterial hypertension (PAH). In a yet further embodiment, the disease is selected from glaucoma, hereditary hemorrhagic telangiectasia (HHT), proteinuria, wound healing, COPD and asthma.

Thus, as a further embodiment, the present invention provides the use of a compound of formula (I) or a pharmaceutically acceptable salt thereof for the manufacture of a medicament. In a further embodiment, the medicament is for treatment of a disease which may be treated inhibition of Smurf-1. In another embodiment, the disease is selected from the afore-mentioned list, suitably Pulmonary Hypertension, including Pulmonary arterial hypertension (PAH), Fibrosis, Rheumatoid Arthritis, and Fracture healing; more suitably Pulmonary arterial hypertension (PAH). In a still further embodiment, the disease is selected from glaucoma, hereditary hemorrhagic telangiectasia (HHT), proteinuria, wound healing, COPD and asthma.

In one embodiment of the present invention, there is provided 1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide, or a pharmaceutically acceptable salt or co-crystal thereof, for use in the treatment of Pulmonary Hypertension, including Pulmonary arterial hypertension (PAH), Fibrosis, Rheumatoid Arthritis, and Fracture healing.

In another embodiment of the present invention, there is provided 1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide, or a pharmaceutically acceptable salt thereof, for use in the treatment of glaucoma, hereditary hemorrhagic telangiectasia (HHT), proteinuria, wound healing, COPD and asthma.

In another embodiment of the present invention, there is provided 1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide, or a pharmaceutically acceptable salt or co-crystal thereof, for use in the treatment of Pulmonary Hypertension, including Pulmonary arterial hypertension (PAH), Fibrosis, Rheumatoid Arthritis, and Fracture healing.

In another embodiment of the present invention, there is provided 1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide, or a pharmaceutically acceptable salt thereof, for use in the treatment of glaucoma, hereditary hemorrhagic telangiectasia (HHT), proteinuria, wound healing, COPD and asthma.

In another embodiment of the present invention, there is provided 1-(2-Chloro-4-cyclopropylphenyl)-N-(2-cyclohexyl-1-methyl-d$_3$,5-methyl-3-oxo-2,3-dihydro-1H-pyrazol-4-yl)-5-methyl-1H-1,2,3-triazole-4-carboxamide, or a pharmaceutically acceptable salt or co-crystal thereof, for use in the treatment of Pulmonary Hypertension, including Pulmonary arterial hypertension (PAH), Fibrosis, Rheumatoid Arthritis, and Fracture healing.

In another embodiment of the present invention, there is provided 1-(2-Chloro-4-cyclopropylphenyl)-N-(2-cyclohexyl-1-methyl-d$_3$,5-methyl-3-oxo-2,3-dihydro-1H-pyrazol-4-yl)-5-methyl-1H-1,2,3-triazole-4-carboxamide, or a pharmaceutically acceptable salt thereof, for use in the treatment of glaucoma, hereditary hemorrhagic telangiectasia (HHT), proteinuria, wound healing, COPD and asthma.

In another embodiment of the present invention, there is provided N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide, or a pharmaceutically acceptable salt or co-crystal thereof, for use in the treatment of Pulmonary Hypertension, including Pulmonary arterial hypertension (PAH), Fibrosis, Rheumatoid Arthritis, and Fracture healing.

In another embodiment of the present invention, there is provided N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide, or a pharmaceutically acceptable salt thereof, for use in the treatment of glaucoma, hereditary hemorrhagic telangiectasia (HHT), proteinuria, wound healing, COPD and asthma.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

Pharmaceutical Assay

Compounds of the invention and their pharmaceutically acceptable salts, hereinafter referred to alternatively as "agents of the invention", are useful as pharmaceuticals. In particular, the compounds are selective Smurf-1 inhibitors, and may be tested in the following assays.

To determine the HECT E3 ligase selectivity of the compounds, a panel of biochemical HECT E3 ligase autoubiquitinylation assays was employed (Smurf-1, Smurf-2, VWVP1, VWVP2, ITCH, Nedd4, Nedd4L and E6AP). The conjugation of ubiquitin to a protein substrate is a multistep process. In an initial ATP-requiring step, a thioester bond is formed between the carboxyl terminus of ubiquitin and an internal cystein residue of the ubiquitin-activating enzyme (E1). Activated ubiquitin is then transferred to a specific cystein residue of an ubiquitin-conjugating enzyme (E2). E2s donate ubiquitin to a HECT E3 ligase (E3) from which it is transferred to the substrate protein. HECT E3 ligases can auto-ubiquitinylate. This event is detected in the TR-FRET (Time-Resolved Fluorescence Resonance Energy Transfer) assay used in this panel. The reaction mix contains E1, E2, tagged-E3, biotin-conjugated ubiquitin, the compound and ATP in a suitable buffer and is incubated for 45 minutes to allow auto-ubiquitinylation of the E3 ligase. To measure the extent of ubiquitinylated E3 ligase by TR-FRET, the donor fluorophore Europium cryptate (Eu3+ cryptate), conjugated to streptavidin which subsequently binds to biotinylated ubiquitin, and the modified allophycocyanin XL665 (HTRF® primary acceptor fluorophore) coupled to a tag-specific antibody (HA, His or GST), which recognizes the respective E3 ligase fusion proteins, are added after the reaction is complete. When these two fluorophores are brought together by a biomolecular interaction (in this case ubiquitinylation of the E3 ligase), a portion of the energy captured by the Cryptate during excitation is released through fluorescence emission at 620 nm, while the remaining energy is transferred to XL665. This energy is then released by XL665 as specific fluorescence at 665 nm. Light at 665 nm is emitted only through FRET with Europium. Because Europium Cryptate is present in the assay, light at 620 nm is detected even when the biomolecular interaction does not bring XL665 within close proximity.

Autoubiquitinylation of Smurf-1 in cells leads to the proteasomal degradation of Smurf-1. Therefore, inhibition of the Smurf-1 catalytic domain abolishes Smurf-1 autoubiquitinylation and degradation, leading to accumulation of inhibited Smurf-1 protein in the cell.

Cellular activity of compounds at the Smurf-1 HECT domain is assessed by measuring the accumulation of Smurf-1 protein in HEK293 cells stably expressing Prolabel-tagged Smurf-1 under the control of a tetracycline-inducible promoter, using the DiscoverX PathHunter Pro-Label Detection Kit. This technology measures the amount of Prolabel-tagged Smurf-1 in an enzyme complementation assay of the cell lysate. In this approach, a small 4 kDa complementing fragment of beta-galactosidase, called Pro-Label, is expressed as an N-terminal fusion with human Smurf-1. This tag is the enzyme donor (ED) and enables detection of target protein levels after complementation with the larger portion of beta-galactosidase, termed EA for enzyme acceptor, to form functional beta-galactosidase enzyme. EA is exogenously added to the cell lysates. The enzyme activity is measured using a chemiluminescent substrate and is proportional to the amount of reconstituted enzyme and hence Smurf-1 levels.

Test and reference compounds are prepared at 180× [final] in 90% DMSO, and diluted 1:3 in 90% DMSO.

For the biochemical assay panel, 50 nl of the test compounds, reference compounds and buffer/DMSO control are transferred to the respective wells of a 384-well white GREINER "SMALL VOLUME" PS plate. The assay panel is run at room temperature on a Biomek FX liquid handling workstation. To the assay plates containing 50 nl compound or control solutions in 90% DMSO, 4.5 ul of E3 ligase solution were added per well, followed by 4.5 ul of the pre-incubated E1/E2/Ub mix or the pre-diluted ubiquitin (LOW control). Plates are shaken vigorously after each addition. In this assay the compound concentrations range from 3 nM to 10 uM in an 8-point dose-response curve.

After 45 min of incubation the ubiquitinylation reactions were stopped by adding 4.5 ul 2 mM NEM, immediately followed by 4.5 ul of a detection solution including the XL665-labeled antibody and the streptavidin-coupled europium to give a total volume of 18 ul. After an incubation time of 45 min in the dark, the plates are transferred into the Pherastar fluorescence reader to measure the TR-FRET signal.

For the cellular assay 250 nl of the test compounds, reference compounds and buffer/DMSO control are then transferred to the respective wells of a sterile 120 ul 384-well white GREINER PS, CELLSTAR, uClear tissue culture plate. To distribute the compound solution evenly in the medium before adding the cells, 10 ul of cell culture medium are added to each well of the compound containing plate using the MULTIDROP 384 dispenser and shaken vigorously. Cells are detached from the flask after a short incubation with trypsin-EDTA, counted and diluted to a concentration of $1.5 \times 10^6$ cells/ml in culture medium. The expression of Smurf-1 is induced by adding doxycyline to a final concentration of 0.2 ug/ml. 10 ul of the cell suspension are added to each well of the compound-containing plates by using the MULTIDROP 384 dispenser. The plates are incubated over night at 37° C., 5% $CO_2$. In this assay the compound concentrations range from 6.75 nM to 22.5 uM in an 8-point dose-response curve.

After overnight incubation with the compounds the levels of Smurf-1 are determined using the PathHunter Prolabel detection kit from DiscoverX. First 10 ul of a lysis/CL detection working solution are added manually using a multi-channel step-pipettor, followed by the addition of 5 ul enzyme acceptor EA. The plates are mixed on a plate shaker and incubated for 2-3 hours at room-temperature before measuring the chemiluminescent signal in the PherStar plate reader.

Compounds of the Examples, herein below, have Smurf-1 $IC_{50}$ values in the data measurements described above as shown in Table A.

TABLE A

| Example | Smurf-1/IC50 nM |
|---------|-----------------|
| 1 | 440 |
| 2 | 570 |
| 3 | 890 |

TABLE A-continued

| Example | Smurf-1/IC50 nM |
|---------|-----------------|
| 4 | 1200 |
| 5 | 550 |
| 6 | 8200 |
| 7 | 5800 |
| 8 | 2800 |
| 9 | 4400 |
| 10 | 92 |
| 11 | 1000 |
| 12 | 98 |
| 13 | 3300 |
| 14 | 230 |
| 15 | 4500 |
| 16 | 55 |
| 17 | 3100 |

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) or a pharmaceutically acceptable salt thereof and at least one other therapeutic agent as a combined preparation for simultaneous, separate or sequential use in therapy. In one embodiment, the therapy is the treatment of a disease or condition mediated by Smurf-1. Products provided as a combined preparation include a composition comprising the compound of formula (I) or a pharmaceutically acceptable salt thereof and the other therapeutic agent(s) together in the same pharmaceutical composition, or the compound of formula (I) or a pharmaceutically acceptable salt thereof and the other therapeutic agent(s) in separate form, e.g. in the form of a kit.

In one embodiment, the invention provides a pharmaceutical composition comprising a compound of formula (I) or a pharmaceutically acceptable salt thereof and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I) or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) or a pharmaceutically acceptable salt thereof for treating a disease or condition mediated by Smurf-1], wherein the medicament is prepared for administration with another therapeutic agent. The invention also provides the use of another therapeutic agent for treating a disease or condition mediated by Smurf-1, wherein the medicament is administered with a compound of formula (I) or a pharmaceutically acceptable salt thereof.

The invention also provides a compound of formula (I) or a pharmaceutically acceptable salt thereof for use in a method of treating a disease or condition mediated by Smurf-1, wherein the compound of formula (I) or a pharmaceutically acceptable salt thereof is prepared for administration with another therapeutic agent. The invention also provides another therapeutic agent for use in a method of treating a disease or condition mediated by Smurf-1, wherein the other therapeutic agent is prepared for administration with a compound of formula (I) or a pharmaceutically acceptable salt thereof. The invention also provides a compound of formula (I) or a pharmaceutically acceptable salt thereof for use in a method of treating a disease or condition mediated by Smurf-1, wherein the compound of formula (I) or a pharmaceutically acceptable salt thereof is administered with another therapeutic agent. The invention also provides another therapeutic agent for use in a method of treating a disease or condition mediated by Smurf-1, wherein the other therapeutic agent is administered with a compound of formula (I) or a pharmaceutically acceptable salt thereof.

The invention also provides the use of a compound of formula (I) or a pharmaceutically acceptable salt thereof for treating a disease or condition mediated by Smurf-1, wherein the patient has previously (e.g. within 24 hours) been treated with another therapeutic agent. The invention also provides the use of another therapeutic agent for treating a disease or condition mediated by Smurf-1, wherein the patient has previously (e.g. within 24 hours) been treated with a compound of formula (I) or a pharmaceutically acceptable salt thereof.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

General Conditions:

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer [M+H]+ refers to protonated molecular ion of the chemical species.

NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

Instrumentation

MS Methods: Using Agilent 1100 HPLC systems with an Agilent 6110 Mass Spectrometer LowpH v002

Column Phenomenex Gemini C18 50×4.6 mm, 3.0 μm
Column Temperature 50° C.
Eluents A: $H_2O$, B: methanol, both containing 0.1% TFA
Flow Rate 1.0 ml/min
Gradient 5% to 95% B in 2.0 min, 0.2 min 95% B 2 minLC v003

Column Waters BEH C18 50×2.1 mm, 1.7 μm
Column Temperature 50° C.
Eluents A: $H_2O$, B: acetonitrile, both containing 0.1% TFA
Flow Rate 0.8 ml/min
Gradient 0.20 min 5% B; 5% to 95% B in 1.30 min, 0.25 min 95% B 8 minLowpHv01:

Column: Waters Acquity CSH 1.7 μm, 2.1×100 mm
Temperature: 50° C.
Mobile Phase: A: Water+0.1% Formic Acid B: Acetonitrile+0.1% Formic Acid
Flow rate: 0.7 mL/min
Gradient: 0.0 min 2% B, 0.3-6.5 min 2-98% B, 6.5-7.5 min 98% B, 7.5-8.0 min 5-98% B 2 minLowpH:

Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.3 min 5-98% B, 1.3-1.55 min 98% B, 1.55-1.6 min 98-5% B 2 minLowpH01:

Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B 2 minLowpH03:

Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.8 min 5-98% B, 1.8-2.1 min 98% B, 2.1-2.3 min 98% B 2 minHighpHv03:

Column: Waters Acquity CSH 1.7 μm, 2.1×50 mm
Temperature: 50° C.
Mobile Phase: A: Water+0.1% Ammonia B: Acetonitrile+0.1% Ammonia
Flow rate: 1.0 mL/min
Gradient: 0.0 min 5% B, 0.2-1.8 min 5-98% B, 1.8-2.1 min 98% B, 2.1-2.3 min 98-5% B 10 minLowpHv01:
Column: Waters Acquity CSH 1.7 μm, 2.1×100 mm
Temperature: 50° C.
Mobile Phase: A: Water+0.1% Formic Acid B: Acetonitrile+ 0.1% Formic Acid
Flow rate: 0.7 mL/min
Gradient: 0.0 min 2% B, 0.5-8.0 min 2-98% B, 8.0-9.0 min 98% B, 9.0-9.1 min 98-2% B
LCMS (SRPb)
Column: Acquity HSS T3 2.1×50 mm, 1.8 micron
Column Temperature: 60° C.
Eluents: A: $H_2O$ (0.05% formic acid, 3.75 mM ammonium acetate)
B: acetonitrile (0.05% formic acid)
Flow Rate: 1.0 ml/min
Gradient 5% to 98% in 1.4 min Abbreviations aq aqueous
br broad
d doublet
dd doublet of doublets
DCM dichloromethane
DMF N,N-dimethylformamide
DMSO dimethylsulfoxide
$Et_3N$ triethylamine
$Et_2O$ diethylether
EtOAc ethyl acetate
EtOH ethanol
g grams
$H_2$ hydrogen
HCl hydrochloric acid
hr/h hour(s)
ihex iso-hexane
$K_2CO_3$ potassium carbonate
KF potassium fluoride
KOH potassium hydroxide
L liter
LC-MS liquid chromatography and mass spectrometry
MeCN acetonitrile
MeI methyl iodide
MeOH methanol
MS mass spectrometry
mult(s) multiplet(s)
mg milligram
min minutes
ml milliliter
mm millimeter
mmol millimole
m/z mass to charge ratio
$N_2$ nitrogen
$NaHCO_3$ sodium hydrogen carbonate
NaOMe sodium methoxide
$Na_2SO_4$ sodium sulfate
NMR nuclear magnetic resonance
$P(chex)_3$ tricyclohexylphosphine
$Pd(OAc)_2$ palladium (II)acetate
$Pd(Ph_3P)_4$ tetrakis(triphenylphosphine)palladium(0)
ppm parts per million
psi pounds per square inch
q quartet
Rt retention time
RT room temperature
s singlet
sat saturated
$SiCO_3$ silica bound carbonate
t triplet
tt triplet of triplets
TBME methyl tert-butyl ether
TFA trifluoroacetic acid
THF tetrahydrofuran
$TMSN_3$ trimethylsilyl azide
$T_3P$ propylphosphonic anhydride
UV ultra-violet
μL microliter Instrumentation If not indicated otherwise, the analytical conditions are as follows:

LCMS Method A
System: Agilent 1100 Series including Agilent MS1946D with chemical ionization
Column: Waters Symmetry C8 3.5 μm 2×50 mm,
Column Temperature: 50° C.
Eluents: A: $H_2O$, containing 0.1% TFA
B: acetonitrile, containing 0.1% TFA
Flow Rate: 1.0 ml/min
Gradient 0% to 95% B in 2 min LCMS Method B
System: Acquity
Column: Acquity HSS T3 2.1×50 mm, 1.8 micron
Column Temperature: 50° C.
Eluents: A: $H_2O$ (0.05% formic acid, 3.75 mM ammonium acetate)
B: acetonitrile (0.05% formic acid)
Flow Rate: 1.2 ml/min
Gradient 2% to 98% in 1.4 min LCMS Method C
System: Acquity
Column: Acquity HSS T3 2.1×50 mm, 1.8 micron
Column Temperature: 60° C.
Eluents: A: $H_2O$ (0.05% formic acid, 3.75 mM ammonium acetate)
B: acetonitrile (0.05% formic acid)
Flow Rate: 1.0 ml/min
Gradient 5% to 98% in 1.4 min HPLC Method D
System: Agilent 1200 HPLC
Column: Zorbax Eclipse XDB-C18 4.6×50 mm, 1.8 micron
Column Temperature: 35° C.
Eluents: A: $H_2O$, containing 0.1% TFA
B: acetonitrile, containing 0.1% TFA
Flow Rate: 1.0 ml/min
Gradient 5% to 100% B in 7.5 min Prep Method E
System: Waters
Column: Water Sunfire C18, 150×30 mm, 5 micron
Eluents: A: $H_2O$, containing 0.1% TFA
B: acetonitrile, containing 0.1% TFA
Flow Rate: 30-50 ml/min
Gradient 40% to 80% B in 7.25 min Prep Method F
System: Waters
Column: Xselect CSH Prep C18, 100×30 mm, 5 micron
Eluents: A: $H_2O$, containing 0.1% TFA
B: acetonitrile, containing 0.1% TFA
Flow Rate: 30-50 ml/min
Gradient 40% to 80% B in 9.5 min Prep Method G
Column: Sunfire column 30×100 mm, C18, 5 um
Column Temperature: 50° C.
Eluents: A: H₂O (0.1% TFA)
    B: Acetonitrile (0.1% TFA)
Gradient 30% to 70% B
LCMS Method H
System: Shimadzu LCMS 2010 series
Column: Xtimate C18, 3 um, 2.1*30 mm
Column Temperature: 50° C.
Eluents: A: H₂O (1.5 mlTFA in 4 L)
    B: Acetonitrile (0.75 mlTFA in 4 L)
Flow Rate: 1.2 ml/min
Gradient 10% to 80% B in 1.5 mins
HPLC Method I
System: Shimadzu LCMS 2010HT series or 10A, 20AB series
Column: Xbridge shieldRP18, 5 um, 50 mm*2.1 mm
Column Temperature: 40° C.
Eluents: A: H₂O (2 mL NH₃OH in 4 L)
    B: Acetonitrile
Flow Rate: 1.2 ml/min
Gradient 10% to 80% B in 6 mins
Method 2 minLowpH
System: Acquity
Column: Acquity CSH C18 50×2.1 mm
Column Temperature: 50° C.
Eluents: A: H₂O, containing 0.1% formic acid
    B: acetonitrile, containing 0.1% formic acid
Flow Rate: 1.0 ml/min
Gradient 0% to 98% B in 1.55 min
Method 2 minLowpHvOl
System: Acquity
Column: Acquity CSH C18 50×2.1 mm
Column Temperature: 50° C.
Eluents: A: H₂O, containing 0.1% formic acid
    B: acetonitrile, containing 0.1% formic acid
Flow Rate: 1.0 ml/min
Gradient 0% to 98% B in 1.75 min
Method 10 minLowpHv01
System: Acquity
Column: Acquity CSH C18 100×2.1 mm
Column Temperature: 50° C.
Eluents: A: H₂O, containing 0.1% formic acid
    B: acetonitrile, containing 0.1% formic acid
Flow Rate: 0.7 ml/min
Gradient 0% to 98% B in 9 min
Method 2 minLowpHv02
System: Acquity
Column: Acquity CSH C18 50×2.1 mm
Column Temperature: 50° C.
Eluents: A: H₂O, containing 0.1% TFA
    B: acetonitrile, containing 0.1% TFA
Flow Rate: 1.0 ml/min
Gradient 0% to 98% B in 1.75 min
Method 2 minLowpHv03
System: Acquity
Column: Acquity CSH C18 50×2.1 mm
Column Temperature: 50° C.
Eluents: A: H₂O, containing 0.1% formic acid
    B: acetonitrile, containing 0.1% formic acid
Flow Rate: 1.0 ml/min
Gradient 0% to 98% B in 2.1 min

PREPARATION OF FINAL COMPOUNDS

Example 1

1-(2-Chloro-4-methoxyphenyl)-N-(2-cyclohexyl-1,5-dimethyl-3-oxo-2,3-dihydro-1H-pyrazol-4-yl)-5-methyl-1H-1,2,3-triazole-4-carboxamide

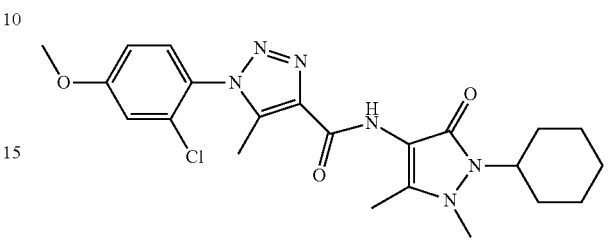

Step 1: 1-Azido-2-chloro-4-methoxybenzene A solution of 2-chloro-4-methoxyaniline (200 mg, 1.269 mmol) in acetic acid (15 ml) and water (15 ml) was stirred and cooled in an ice bath. A solution of sodium nitrite (88 mg, 1.269 mmol) in water (2 ml) was added dropwise and the mixture was stirred for 10 mins under ice cooling. A solution of sodium azide (83 mg, 1.269 mmol) in water (2 ml) was added dropwise and the mixture was stirred under ice cooling for 5 mins and then at RT for 30 mins. To the resulting mixture was added 2M NaOH (aq) until basic and this was extracted with diethylether (2×). The organic extracts were dried over MgSO₄, filtered and concentrated under vacuum to give the title compound as a brown solid.
LC-MS: Rt 1.23 mins; MS m/z no mass ion [M+H]⁺; Method 2 minLowpHv01
¹H NMR (400 MHz, DMSO-d6) δ 7.34 (1H, d), 7.12 (1H, d), 7.01 (1H, dd), 3.77 (3H, s).
Step 2: 1-(2-Chloro-4-methoxyphenyl)-5-methyl-1H-1,2,3-triazole-4-carboxylic acid To a stirred solution of 1-azido-2-chloro-4-methoxybenzene (162 mg, 0.882 mmol) and methyl 3-oxobutanoate (0.286 ml, 2.65 mmol) in MeOH (10 ml) was added sodium methoxide (5M in MeOH) (1.059 ml, 5.29 mmol) dropwise and the mixture was heated at 50° C. for 16 hrs. The resulting mixture was diluted with water, washed with diethylether (2×) and the organic extracts discarded. To the aqueous layer was added 5M HCl (aq) until acidic and the solid that crashed out was collected by filtration, washed with water and dried on the vacuum line to yield the title compound as an off-white solid.
LC-MS: Rt 0.93 mins; MS m/z 268.1 [M+H]⁺; Method 2 minLowpHv01
¹H NMR (400 MHz, DMSO-d6) δ 13.2 (1H, br s), 7.63 (1H, d), 7.39 (1H, d), 7.17 (1H, dd), 3.89 (3H, s), 2.32 (3H, s).
Step 3: 1-(2-Chloro-4-methoxyphenyl)-N-(2-cyclohexyl-1,5-dimethyl-3-oxo-2,3-dihydro-1H-pyrazol-4-yl)-5-methyl-1H-1,2,3-triazole-4-carboxamide
To a solution of oxalyl chloride (63 μl, 0.717 mmol) and DMF (74 μl, 0.956 mmol) in dry DCM (2 ml) under nitrogen was added 1-(2-chloro-4-methoxyphenyl)-5-methyl-1H-1,2,3-triazole-4-carboxylic acid (115 mg, 0.430 mmol) and the mixture was stirred at RT for 1 hr. A solution of 4-amino-2-cyclohexyl-1,5-dimethyl-1H-pyrazol-3(2H)-one (Intermediate A) (100 mg, 0.478 mmol) in dry DCM (1 ml) was added followed by triethylamine (0.200 ml, 1.433 mmol) and the reaction mixture was stirred at RT for 48 hrs.

The resulting mixture was loaded onto a pre-wet (MeOH) 1 g ISOLUTE® PE-AX/SCX-2 cartridge and washed with MeOH, collecting the eluent. The eluent was concentrated under reduced pressure and the resulting residue was dissolved in DMSO (0.9 ml) and purified by reverse phase chromatography (Prep Method E). The product fraction was concentrated under reduced pressure, diluted with sat. NaHCO$_3$ (aq) and extracted with DCM. The organic extract was passed through a phase separating cartridge and the eluent was concentrated under reduced pressure to give the title compound.

LC-MS: Rt 4.44 mins; MS m/z 461.2 [M+H]$^+$; Method 10 minLowpHv01

$^1$H NMR (400 MHz, CDCl$_3$) δ 8.36 (1H, s), 7.32 (1H, d), 7.13 (1H, d), 6.98 (1H, dd), 4.06 (1H, mult), 3.90 (3H, s), 3.24 (3H, s), 2.46 (3H, s), 2.23 (3H, s), 1.99 (2H, mults), 1.87 (4H, mults), 1.70 (1H, mult), 1.37 (2H, mults), 1.23 (1H, mult).

Example 2

N-(2-Cyclohexyl-1,5-dimethyl-3-oxo-2,3-dihydro-1H-pyrazol-4-yl)-1-(2,4-dichlorophenyl)-5-methyl-1H-1,2,3-triazole-4-carboxamide

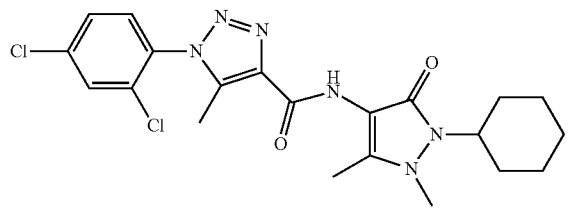 [SMILES: Cc1c(C(=O)Nc2c(C)n(C)n(C3CCCCC3)c2=O)nnn1-c1ccc(Cl)cc1Cl]

The title compound was prepared analogously to Example 1 by replacing 2-chloro-4-methoxyaniline (step 1) with 2,4-dichloroaniline;

LC-MS: Rt 4.71 mins; MS m/z 463.2 [M+H]$^+$; Method 10 minLowpHv01

$^1$H NMR (400 MHz, CDCl3) δ 8.35 (1H, s), 7.66 (1H, d), 7.49 (1H, dd), 7.38 (1H, d), 4.06 (1H, mult), 3.24 (3H, s), 2.48 (3H, s), 2.23 (3H, s), 1.99 (2H, mults), 1.87 (4H, mults), 1.70 (1H, mult), 1.37 (2H, mults), 1.22 (1H, mult).

Example 3

N-(2-Cyclohexyl-1,5-dimethyl-3-oxo-2,3-dihydro-1H-pyrazol-4-yl)-1-(4-methoxy-2-(trifluoromethyl)phenyl)-5-methyl-1H-1,2,3-triazole-4-carboxamide

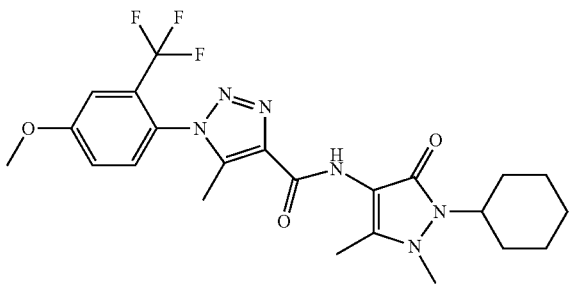 [SMILES: COc1ccc(-n2nnc(C(=O)Nc3c(C)n(C)n(C4CCCCC4)c3=O)c2C)c(C(F)(F)F)c1]

The title compound was prepared analogously to Example 1 by replacing 2-chloro-4-methoxyaniline (step 1) with 4-methoxy-2-(trifluoromethyl)aniline.

LC-MS: Rt 4.57 mins; MS m/z 493.3 [M+H]$^+$; Method 10 minLowpHv01

$^1$H NMR (400 MHz, CDCl3) δ 8.38 (1H, s), 7.39 (1H, d), 7.30 (1H, d), 7.23 (1H, dd), 4.07 (1H, mult), 3.97 (3H, s), 3.25 (3H, s), 2.42 (3H, s), 2.24 (3H, s), 2.01 (3H, mults), 1.88 (2H, mults), 1.69 (2H, mults), 1.38 (2H, mults), 1.24 (1H, mult).

Example 4

N-(2-Cyclohexyl-1,5-dimethyl-3-oxo-2,3-dihydro-1H-pyrazol-4-yl)-1-(4-methoxy-3-methylphenyl)-5-methyl-1H-1,2,3-triazole-4-carboxamide

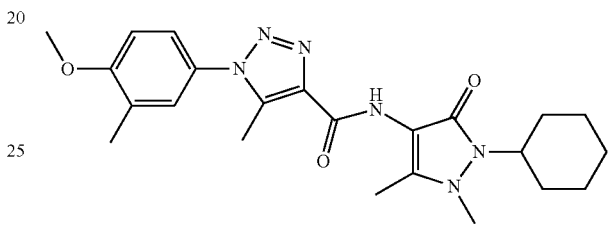

The title compound was prepared analogously to Example 1 by replacing 2-chloro-4-methoxyaniline (step 1) with 4-methoxy-3-methylaniline.

LC-MS: Rt 4.47 mins; MS m/z 440.5 [M+H]$^+$; Method 10 minLowpHv01

$^1$H NMR (400 MHz, CDCl3) δ 8.36 (1H,$), 7.22 (2H, mults), 6.95 (1H, mult), 4.05 (1H, mult), 3.91 (3H, s), 3.22 (3H, s), 2.57 (3H, s), 2.28 (3H, s), 2.22 (3H, s), 1.99 (2H, mults), 1.86 (4H, mults), 1.69 (1H, mults), 1.37 (2H, mults), 1.22 (1H, mult).

Example 5

1-(2-Chloro-4-(trifluoromethoxy)phenyl)-N-(2-cyclohexyl-1,5-dimethyl-3-oxo-2,3-dihydro-1H-pyrazol-4-yl)-5-methyl-1H-1,2,3-triazole-4-carboxamide

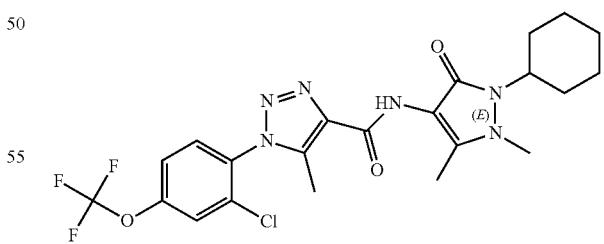

The title compound was prepared analogously to Example 1 by replacing 2-chloro-4-methoxyaniline (step 1) with 2-chloro-4-trifluormethoxyaniline. Purification was carried out by reverse phase chromatography using Prep Method G.

LC-MS: Rt: 2.10 min; MS m/z 513 [M+H]$^+$; Method A $^1$H-NMR (400 MHz, DMSO-d$_6$) δ 9.35 (1H, s), 8.02 (1H, d), 7.93 (1H, d), 7.70 (1H, mult), 3.96 (1H, mult), 3.24 (3H, s), 2.36 (3H, s), 2.05 (3H, s), 2.05-1.94 (2H, mults), 1.79-1.76 (2H, mults), 1.69-1.59 (3H, mults), 1.36-1.26 (2H, mults), 1.19-1.13 (1H, mult).

Example 6

1-(4-Chlorophenyl)-N-(2-cyclohexyl-1,5-dimethyl-3-oxo-2,3-dihydro-1H-pyrazol-4-yl)-5-methyl-1H-1,2,3-triazole-4-carboxamide

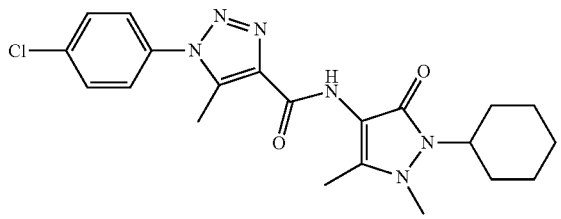 [SMILES: Cc1c(C(=O)Nc2c(C)n(C)n(C3CCCCC3)c2=O)nnn1-c1ccc(Cl)cc1]

The title compound was prepared analogously to Example 1 by replacing 1-azido-2-chloro-4-methoxybenzene (step 2) with 1-azido-4-chlorobenzene in (0.5 M in TBME).

LC-MS: Rt 4.40 mins; MS m/z 431.1 [M+H]$^+$; Method 10 minLowpHv01

$^1$H NMR (400 MHz, CDCl3) δ 8.36 (1H, s), 7.57 (2H, mults), 7.43 (2H, mults), 4.05 (1H, mult), 3.23 (3H, s), 2.62 (3H, s), 2.22 (3H, s), 1.99 (3H, mults), 1.87 (4H, mults), 1.70 (1H, mult), 1.37 (2H, mults), 1.22 (1H, mult).

Example 7

1-(2,4-Dichlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide

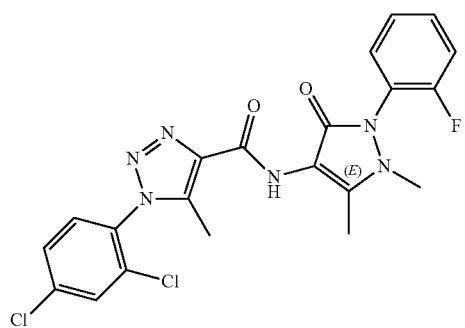 [SMILES: Cc1c(C(=O)Nc2c(C)n(C)n(-c3ccccc3F)c2=O)nnn1-c1ccc(Cl)cc1Cl]

Steps 1-2: 1-(2,4-Dichlorophenyl)-5-methyl-1H-1,2,3-triazole-4-carboxylic acid The title compound was prepared analogously to 1-(2-chloro-4-methoxyphenyl)-5-methyl-1H-1,2,3-triazole-4-carboxylic acid (Example 1 steps 1 and 2) by replacing 2-chloro-4-methoxyaniline (Example step 1) with 2, 4-dichloroaniline.

LCMS: Rt 4.10 mins; MS m/z 274.0 [M+H]+; Method 10minLowpHv01

Step 3: 1-(2,4-Dichlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide A solution of 1-(2,4-dichlorophenyl)-5-methyl-1H-1,2,3-triazole-4-carboxylic acid (100 mg, 0.368 mmol), oxalyl chloride (0.048 ml, 0.551 mmol) and DMF (0.057 ml, 0.735 mmol) in DCM (5 ml) was stirred at RT for 15 mins. 4-Amino-2-(2-fluorophenyl)-1,5-dimethyl-1H-pyrazol-3 (2H)-one (Intermediate B) (89 mg, 0.404 mmol) was added followed by triethylamine (0.154 ml, 1.103 mmol) and the mixture was stirred at RT for 30 mins. The resulting mixture was diluted with DCM, washed with 0.1M HCl(aq) and sat. NaHCO$_3$(aq) and the organic extracts were passed through a phase separating cartridge and concentrated under reduced pressure. The resultant brown oil was absorbed onto silica and purified by chromatography eluting with 0-10% MeOH in TBME. The product fractions were combined and concentrated under reduced pressure to give a pale pink solid which was triturated with diethylether. The resulting solid was collected by filtration and dried in the vacuum oven to give the title compound as a pale pink solid.

LC-MS: Rt 4.33 mins; MS m/z 475.3 [M+H]$^+$; Method 10 minLowpHv01

$^1$H NMR (400 MHz, DMSO-d6) δ 9.57 (1H, s), 8.08 (1H, d), 7.83 (1H, d), 7.77 (1H, dd), 7.56-7.35 (4H, mults), 3.09 (3H, s), 2.39 (3H, s), 2.20 (3H. s).

Example 8

1-(4-Chlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide

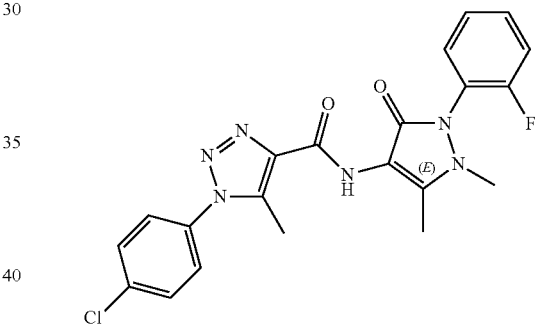

Step 1: 1-(4-Chlorophenyl)-5-methyl-1H-1,2,3-triazole-4-carboxylic acid

The title compound was prepared analogously to 1-(2-chloro-4-methoxyphenyl)-5-methyl-1H-1,2,3-triazole-4-carboxylic acid (Example 1 step 2) by replacing 1-azido-2-chloro-4-methoxybenzene with 1-azido-4-chlorobenzene in (0.5 M in TBME).

LCMS: Rt 0.86 mins; MS m/z 240.1 [M+H]+; Method 2 minLowpH

Step 2: 1-(4-Chlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide To a stirred solution of 1-(4-chlorophenyl)-5-methyl-1H-1,2,3-triazole-4-carboxylic acid (100 mg, 0.421 mmol), oxalyl chloride (0.041 ml, 0.463 mmol) and DMF (0.065 ml, 0.842 mmol) in dry DCM (5 ml) was added a solution of 4-amino-2-(2-fluorophenyl)-1,5-dimethyl-1H-pyrazol-3 (2H)-one (Intermediate B) (102 mg, 0.463 mmol) in dry DCM (1 ml), followed by triethylamine (0.176 ml, 1.262 mmol) and the mixture was stirred at RT for 1 hr. The resulting mixture was diluted with DCM and washed with 0.1M HCl(aq) and sat. NaHCO$_3$(aq). The organic extracts were passed through a phase separating cartridge and concentrated under reduced pressure. The resulting solid was absorbed onto silica and purified by chromatography eluting with 0-10% MeOH in TBME. The product fractions were combined and concentrated under reduced pressure to give a glassy solid, which was suspended in 1:1 iso-hexane:Et₂O, heated at 50° C. for 2 h, stoppered and allowed to cool for 16 hrs. The solid was collected by filtration and dried on the vacuum line to give the title compound as a pale yellow solid.

LC-MS: Rt 4.04 mins; MS m/z 441.4 [M+H]⁺; Method 10 minLowpHv01

¹H NMR (400 MHz, DMSO-d6) δ 9.51 (1H, s), 7.75-7.70 (4H, mults), 7.53 (1H, mult), 7.47-7.35 (3H, mults), 3.08 (3H, s), 2.55 (3H, s), 2.19 (3H, s).

Example 9

1-(2-Chloro-4-(trifluoromethoxy)phenyl)-N-(2-(2-fluorophenyl)-1,5-dimethyl-3-oxo-2,3-dihydro-1H-pyrazol-4-yl)-5-methyl-1H-1,2,3-triazole-4-carboxamide

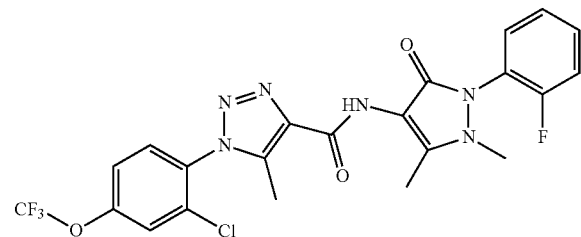 [SMILES: Cc1c(C(=O)Nc2c(C)n(C)n(-c3ccccc3F)c2=O)nnn1-c1ccc(OC(F)(F)F)cc1Cl]

Steps 1-2: 1-(2-Chloro-4-(trifluoromethoxy)phenyl)-5-methyl-1H-1,2,3-triazole-4-carboxylic acid The title compound was prepared analogously to 1-(2-chloro-4-methoxyphenyl)-5-methyl-1H-1,2,3-triazole-4-carboxylic acid (Example step 2) by replacing 2-chloro-4-methoxyaniline (step 1) with 2-chloro-4-trifluormethoxyaniline.

Step 3: 1-(2-Chloro-4-(trifluoromethoxy)phenyl)-N-(2-(2-fluorophenyl)-1,5-dimethyl-3-oxo-2,3-dihydro-1H-pyrazol-4-yl)-5-methyl-1H-1,2,3-triazole-4-carboxamide DMF (43 µL, 0.56 mmol) was dissolved in DCM (1 mL) and cooled to 0° C. Oxalyl chloride (27 µL, 0.308 mmol) was added followed by 1-(2-chloro-4-(trifluoromethoxy)phenyl)-5-methyl-1H-1,2,3-triazole-4-carboxylic acid (90 mg, 0.28 mmol) and the reaction mixture was stirred for 10 min. 4-Amino-2-(2-fluorophenyl)-1,5-dimethyl-1H-pyrazol-3(2H)-one (Intermediate B) (62 mg, 0.28 mmol) was added, followed by triethylamine (117 µL, 0.839 mmol). The reaction was allowed to warm to RT and stirred for 4 h. Saturated aqueous NaHCO₃ was added to the reaction mixture and the product was extracted with DCM. The organic extract was dried and concentrated under reduced pressure. The crude material was purified by reversed phase chromatography (Prep Method G) to afford the title compound.

LC-MS: Rt: 2.08 min; MS m/z 525 [M+H]⁺; Method A

¹H-NMR (400 MHz, DMSO-d₆) δ 9.57 (1H, s), 8.02 (1H, d), 7.94 (1H, d), 7.72-7.69 (1H, mult), 7.52-7.33 (4H, mult), 3.07 (3H, s), 2.38 (3H, s), 2.18 (3H, s).

Example 10

1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide

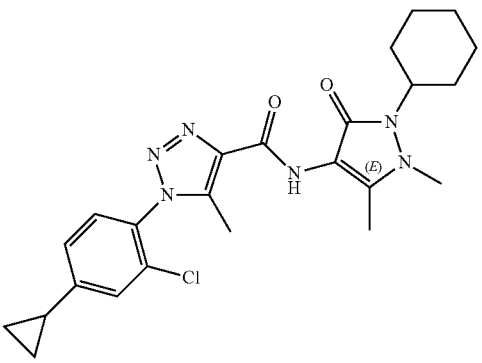 [SMILES: Cc1c(C(=O)Nc2c(C)n(C)n(C3CCCCC3)c2=O)nnn1-c1ccc(C2CC2)cc1Cl]

Step 1: 2-Chloro-4-cyclopropylaniline To toluene (1470 mL) and water (60 mL) under nitrogen was added 4-bromo-2-chloroaniline (63 g, 305 mmol) and cyclopropylboronic acid (26.5 g, 309 mmol). The mixture was cooled and treated with potassium phosphate tribasic (227 g, 1068 mmol) portionwise followed by P(cHex)3 (8.56 g, 30.5 mmol). The flask was flushed with nitrogen, Pd(OAc)₂ (3.56 g, 15.87 mmol) was added and the mixture was heated to 81° C. for 7 hrs then left at RT over the weekend. Further cyclopropylboronic acid (5.5 g, 64 mmol) was added and the mixture was heated to 81° C. for 2 hrs and then cooled to RT. The resulting mixture was diluted with water (600 mL). The aqueous layer was separated and the organic layer was washed with water (300 mL) and brine (300 mL), dried over Na₂SO₄, filtered and evaporated to dryness to give a brown oil. The oil was absorbed onto silica and purified by chromatography eluting with 10-100% EtOAc in heptane. The product fractions were combined and concentrated under reduced pressure to give the title compound as green crystals.

HPLC Method D: Rt 3.94 mins;

¹H NMR (400 MHz, DMSO-d6) δ 6.88 (1H, d), 6.74 (1H, dd), 6.67 (1H, d), 5.06 (2H, br s), 1.78-1.70 (1H, mult), 0.82-0.76 (2H, mults), 0.52-0.47 (2H, mults).

Step 2: 1-Azido-2-chloro-4-cyclopropylbenzene

2-Chloro-4-cyclopropylaniline (70 g, 418 mmol) was dissolved in Me-THF (2090 mL) and cooled to 0° C. in an ice bath. t-Butyl nitrite (59.8 mL, 501 mmol) was added slowly and TMSN₃ (66.5 mL, 501 mmol) dropwise. The mixture was stirred at 0° C. for 30 min and gradually allowed to warm up to RT and stirred for 2 hrs. To the resulting mixture was added sat. NaHCO₃ (aq) (250 mL) slowly under cooling, followed by water (250 mL). The mixture was transferred to a separating funnel and washed with water (1.5 L), dried over Na₂SO₄ and filtered to give the title compound which was used in the next step without further purification;

HPLC Method D: Rt 5.63 mins;

Step 3: 1-(2-Chloro-4-cyclopropylphenyl)-5-methyl-1H-1,2,3-triazole-4-carboxylic acid To crude 1-azido-2-chloro-4-cyclopropylbenzene (0.2 M solution in THF) was added methyl 3-oxobutanoate (146 g, 1254 mmol) and the resulting mixture was cooled to 5° C. NaOMe (232 mL, 1254 mmol) was added slowly forming a precipitate and the mixture was stirred at RT for 64 hrs. The resulting suspension was cooled in an ice bath and water (2 L) was added. The mixture was transferred to a separating funnel and the aqueous layer was extracted with Me-THF (500 mL). The aqueous layer was acidified with 2M HCl (aq) and extracted with EtOAc (2 L) (1×) and (1 L) (2×). The combined organic extracts were washed with water (1 L) and brine (1 L), dried over $Na_2SO_4$, filtered and concentrated under reduced pressure to give an orange oily residue. Water (300 mL) was added and the mixture was stirred for 30 min, filtered, washed with water and dried under reduced pressure to give the title compound as orange crystals.

LC-MS: Rt 0.89 mins; MS m/z 278.1 [M+H]$^+$; Method C $^1$H NMR (400 MHz, DMSO-d6) δ 13.22 (1H, d), 7.55 (1H, d), 7.51 (1H, d), 7.29 (1H, dd), 2.31 (3H, s), 2.08 (1H, mult), 1.10-1.03 (2H, mults), 0.87-0.81 (2H, mults).

Step 4: 1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide 1-(2-Chloro-4-cyclopropylphenyl)-5-methyl-1H-1,2,3-triazole-4-carboxylic acid (15 g, 54.0 mmol) and 4-amino-2-cyclohexyl-1,5-dimethyl-1H-pyrazol-3(2H)-one (Intermediate A)(11.30 g, 54.0 mmol) were slurried in EtOAc (150 mL). The reaction mixture was cooled to 10° C. and triethylamine (18.82 mL, 135 mmol) was added dropwise, followed by dropwise addition of $T_3P$ (50% w/w in EtOAc) (47.7 mL, 81 mmol) over 15 mins, maintaining a temperature <10° C. The reaction mixture was allowed to warm to RT and stirred for 2.5 hrs. The resulting mixture was quenched with sat. sodium bicarbonate (aq) (150 ml). The layers were separated and the organic layer was washed with sat. sodium bicarbonate (aq) (50 ml), water (150 ml) and brine (150 ml). The organic extracts were dried over $MgSO_4$ and charcoal. The desiccant was filtered off and the filtrate was concentrated under reduced pressure. The crude material was slurried in ethyl acetate (335 ml) and heated to reflux with stirring. The hot mixture was filtered and the filtrate was seeded and at left to stand at room temperature overnight. The resulting crystalline solid was collected by filtration and dried under reduced pressure at 40° C. over 2 days to yield the title compound.

LC-MS: Rt 1.32 mins; MS m/z 469.4 & 471.4 [M+H]$^+$; Method 2 minLowpHv03.

$^1$H NMR (400 MHz, DMSO-d6) δ 9.25 (1H, s), 7.59 (1H, d), 7.53 (1H, d), 7.32 (1H, dd), 3.93 (1H, tt), 3.32 (3H, s), 2.34 (3H, s), 2.14-2.07 (1H, m), 2.06 (3H, s), 2.05-1.94 (2H, br m), 1.83-1.75 (2H, br m), 1.71-1.58 (3H, br m), 1.39-1.25 (2H, br m), 1.24-1.12 (1H, br m), 1.09 (2H, m), 0.86 (2H, m).

Example 11

1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide

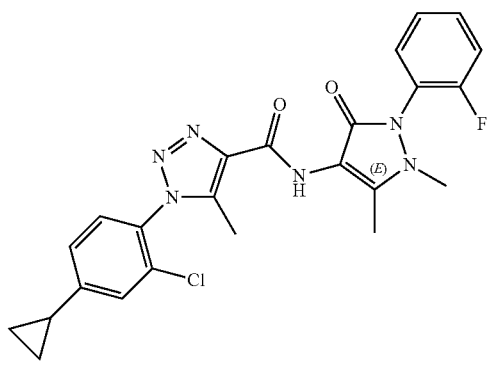 [SMILES: Cc1c(C(=O)Nc2c(C)n(C)n(-c3ccccc3F)c2=O)nnn1-c1ccc(C2CC2)cc1Cl]

A solution of 1-(2-chloro-4-cyclopropylphenyl)-5-methyl-1H-1,2,3-triazole-4-carboxylic acid (Example 10, step 3) (95 mg, 0.342 mmol), oxalyl chloride (0.045 ml, 0.513 mmol) and DMF (0.053 ml, 0.684 mmol) in DCM (5 ml) was stirred at RT for 15 mins. 4-Amino-2-(2-fluorophenyl)-1,5-dimethyl-1H-pyrazol-3(2H)-one (Intermediate B) (83 mg, 0.376 mmol) was added to the mixture followed by triethylamine (0.143 ml, 1.026 mmol) and this was stirred at RT for 30 mins. The resulting mixture was diluted with DCM, washed with 0.1M HCl(aq) and sat. $NaHCO_3$(aq). The organic extracts were passed through a phase separating cartridge and concentrated under reduced pressure to give a brown oil. The oil was absorbed onto silica and purified by chromatography eluting with 0-10% MeOH in TBME. The product fractions were combined and concentrated under reduced pressure to give a yellow glassy solid. The solid was dissolved in 1:1 EtOAc:$Et_2O$, washed with water (2×), brine, dried over $MgSO_4$, filtered and concentrated under reduced pressure to give the title compound as a yellow glassy solid.

LC-MS: Rt 4.60 mins; MS m/z 481.4 [M+H]$^+$; Method 10 minLowpHv01

$^1$H NMR (400 MHz, DMSO-d6) δ 9.53 (1H, s), 7.59 (1H, d), 7.56-7.50 (1H, mult), 7.53 (1H, d), 7.47-7.31 (4H, mults), 3.08 (3H, s), 2.36 (3H, s), 2.20 (3H, s), 2.10 (1H, mult), 1.11-1.06 (2H, mults), 0.89-0.85 (2H, mults).

Example 12

1-(2-Chloro-4-cyclopropylphenyl)-N-(2-cyclohexyl-1-methyl-d$_3$,5-methyl-3-oxo-2,3-dihydro-1H-pyrazol-4-yl)-5-methyl-1H-1,2,3-triazole-4-carboxamide

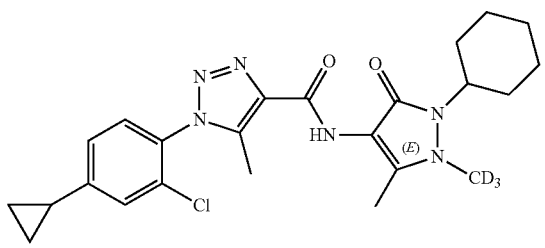 [SMILES: [2H]C([2H])([2H])n1c(C)c(NC(=O)c2nnn(-c3ccc(C4CC4)cc3Cl)c2C)c(=O)n1C1CCCCC1]

To an ice cooled solution of oxalyl chloride (0.033 ml, 0.378 mmol) in DCM (3 ml) was added DMF (0.039 ml, 0.504 mmol) dropwise and the mixture was stirred for 1 hr. To the suspension was added 1-(2-chloro-4-cyclopropylphenyl)-5-methyl-1H-1,2,3-triazole-4-carboxylic acid (Example 10, step 3) (70 mg, 0.252 mmol) and the mixture was stirred at RT under $N_2$ for 1 hr. To the reaction mixture was added (Intermediate C) (53.5 mg, 0.252 mmol) followed by dropwise addition of triethylamine (0.105 ml, 0.756 mmol) and the mixture was stirred at RT for 16 hrs. The resulting mixture was diluted with DCM (20 ml), washed with water (20 ml), 1M HCl (aq) (10 ml) and sat. $NaHCO_3$(aq) (20 ml). The organic extracts were dried over $MgSO_4$, filtered and concentrated under reduced pressure to give the crude product. The crude material was absorbed onto silica and purified by chromatography eluting with 0-90% EtOAc in isohexane, followed by 0-10% MeOH in DCM. The product fractions were combined and concentrated in under reduced pressure to give an orange oil. The oil was dissolved in 1:1 DMSO/MeOH (1 ml) and purified using reverse phase chromatography (Prep Method F). The product fraction was extracted with DCM and the combined organic extracts were concentrated under reduced pressure to give the title compound as a yellow oil.

LC-MS: Rt 1.17 mins; MS m/z 472.4 [M+H]$^+$; Method 2 minLowpHv01

$^1$H NMR (400 MHz, CDCl$_3$) δ 9.25 (1H, s), 7.30 (1H, d), 7.29 (1H, d), 7.16 (1H, d), 4.11 (1H, m), 2.47 (3H, s), 2.26 (3H, s), 2.06-1.96 (3H, m), 1.90 (2H, d), 1.70 (3H, mults), 1.40 (2H, m), 1.28 (1H, m), 1.13 (2H, m), 0.82 (2H, m).

Example 13

1-(4-Chloro-2-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide

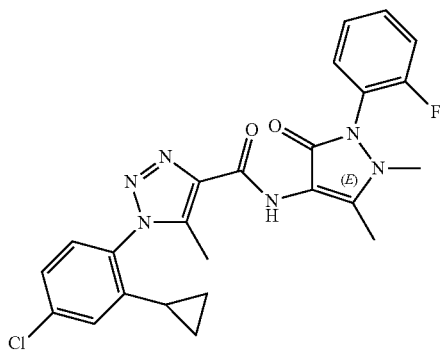 [SMILES: Cc1c(C(=O)Nc2c(C)n(C)n(-c3ccccc3F)c2=O)nnn1-c1ccc(Cl)cc1C1CC1]

Step 1: N-(2-Bromo-4-chlorophenyl)acetamide

A solution of 2-bromo-4-chloroaniline (1 g, 4.84 mmol) in acetic anhydride (5 ml, 4.84 mmol) was stirred at RT for 1.5 hrs. The resulting suspension was collected by filtration and dried on a vacuum line to give the title compound as a white solid.

LC-MS: Rt 0.90 mins; MS m/z 250.0 [M+H]$^+$; Method 2 minLowpH $^1$H NMR (400 MHz, DMSO-d6) δ 9.51 (1H, s), 7.78 (1H, d), 7.62 (1H, d), 7.44 (1H, dd), 2.08 (3H, s).

Step 2: N-(4-Chloro-2-cyclopropylphenyl)acetamide

A mixture of N-(2-bromo-4-chlorophenyl)acetamide (817 mg, 3.29 mmol), cyclopropylboronic acid (706 mg, 8.22 mmol), PdOAc$_2$ (14.76 mg, 0.066 mmol), N-phenyl-2-(di-t-butylphosphino)indole (44.4 mg, 0.132 mmol) and potassium fluoride (955 mg, 16.44 mmol) was stirred in THF (50 ml) at 55° C. for 16 hrs. Further cyclopropylboronic acid (706 mg, 8.22 mmol), PdOAc$_2$ (14.76 mg, 0.066 mmol) and potassium fluoride (955 mg, 16.44 mmol) was added to the reaction mixture and mixture was stirred at 65° C. for 16 hrs. The resulting mixture was diluted with EtOAc and washed with water (2×). The organic extracts were dried over MgSO$_4$, filtered and concentrated under reduced pressure to give a brown solid. The crude product was used in the next step without further purification.

Step 3: 4-Chloro-2-cyclopropylaniline

A suspension of N-(4-chloro-2-cyclopropylphenyl)acetamide (689 mg, 3.29 mmol) in 2M HCl (aq) (25 ml, 823 mmol) was stirred at 100° C. for 3 hrs and then 90° C. for 16 hrs. The resulting mixture was cooled to RT, diluted with EtOAc and water and the layers separated. The organic layer was extracted with 0.1M HCl (aq) and the organic portion was discarded. To the combined aqueous portions was added 2M NaOH (aq) until basic and resulting mixture was extracted with EtOAc (2×). The organic extracts were washed with brine, dried over MgSO$_4$, filtered and concentrated under vacuum to give the title compound as a dark yellow oil.

LC-MS: Rt 0.96 mins; MS m/z 168.1 [M+H]$^+$; Method 2 minLowpH $^1$H NMR (400 MHz, DMSO-d6) δ 6.89 (1H, dd), 6.75 (1H, d), 6.59 (1H, d), 5.11 (2H, s), 1.65 (1H, mult), 0.87-0.81 (2H, mults), 0.51-0.47 (2H, mults).

Step 4: 1-Azido-4-chloro-2-cyclopropylbenzene

A solution of 4-chloro-2-cyclopropylaniline (182 mg, 1.086 mmol) in acetic acid (15 ml) and water (15 ml) was stirred and cooled to 0° C. A solution of sodium nitrite (74.9 mg, 1.086 mmol) in water (1.4 ml) was added dropwise and the mixture was stirred under ice cooling for 10 mins. A solution of sodium azide (70.6 mg, 1.086 mmol) in water (1.5 ml) was added dropwise and was stirred under ice cooling for 1 hr and then at RT 30 mins. To the product mixture was added 2M NaOH (aq) until basic and this was extracted with EtOAc. The organic extract was washed with sat. NaHCO$_3$(aq) and dried over MgSO$_4$, filtered and concentrated under reduced pressure to give the title compound as a dark yellow/brown oil. The crude product was used in the next step without further purification.

Step 5: 1-(4-Chloro-2-cyclopropylphenyl)-5-methyl-1H-1,2,3-triazole-4-carboxylic acid To a stirred solution of 1-azido-4-chloro-2-cyclopropylbenzene (204 mg, 1.054 mmol) and methyl 3-oxobutanoate (0.341 ml, 3.16 mmol) in MeOH (2 ml) was added sodium methoxide (5M in MeOH) (1.264 ml, 6.32 mmol) dropwise and the mixture was stirred at RT for 2.5 h. The mixture was heated at 50° C. for 5 hrs and then left to stir at RT for 16 hrs. The resulting mixture was diluted with water, extracted with diethylether (×2) and the organic extracts were discarded. To the aqueous layer was added 6M HCl (aq) until acidic and this was extracted with diethyl ether. The organic extracts were dried over MgSO$_4$, filtered and concentrated under reduced pressure to yield the title compound as an orange oil.

LC-MS: Rt 0.99 mins; MS m/z 278.4 [M+H]$^+$; Method 2 minLowpH $^1$H NMR (400 MHz, DMSO-d6) δ 13.1 (1H, br s), 7.49-7.48 (2H, mults), 7.23 (1H, br s), 2.35 (3H, s), 1.22 (1H, mult), 0.85-0.83 (2H, mults), 0.77-0.76 (2H, mults).

Step 6: 1-(4-Chloro-2-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide To a stirred solution of oxalyl chloride (0.035 ml, 0.396 mmol) and DMF (0.056 ml, 0.720 mmol) in DCM (10 ml) was added 1-(4-chloro-2-cyclopropylphenyl)-5-methyl-1H-1,2,3-triazole-4-carboxylic acid (100 mg, 0.360 mmol) and the mixture was stirred for 30 mins. Further oxalyl chloride (0.035 ml, 0.396 mmol) was added to the reaction mixture and it was stirred for 1 hr. 4-Amino-2-(2-fluorophenyl)-1,5-dimethyl-1H-pyrazol-3(2H)-one (Intermediate B) (88 mg, 0.396 mmol) was added followed by triethylamine (0.151 ml, 1.080 mmol) and the mixture was stirred at RT for 1 hr. The resulting mixture was diluted with DCM, washed with 0.1M HCl(aq) and sat. NaHCO$_3$(aq). The organic extracts were passed through a phase separating cartridge and concentrated under reduced pressure to give an oil. The oil was absorbed onto silica and purified by chromatography eluting with 0-10% MeOH in TBME. The product fractions were combined and concentrated under reduced pressure to give a yellow glassy solid which was recrystallised from EtOH. The solid was collected by filtration and dried on the vacuum line to give the title compound as a white solid.

LC-MS: Rt 4.63 mins; MS m/z 481.4 [M+H]$^+$; Method 10 minLowpHv01

$^1$H NMR (400 MHz, DMSO-d6) δ 9.51 (1H, s), 7.56-7.35 (6H, mults), 7.24 (1H, d), 3.09 (3H, s), 2.39 (3H, s), 2.20 (3H, s), 1.26 (1H, mult), 0.90-0.85 (2H, mults), 0.82-0.78 (2H, mults).

Example 14

1-(4-Chloro-2-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide

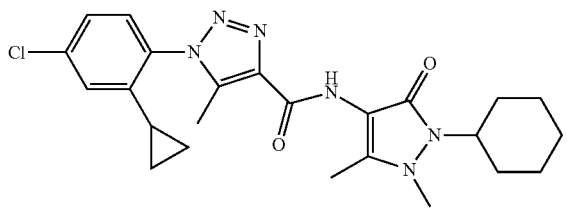 [SMILES: Cc1c(C(=O)Nc2c(C)n(C)n(C3CCCCC3)c2=O)nnn1-c1ccc(Cl)cc1C1CC1]

The title compound was prepared from 1-(4-chloro-2-cyclopropylphenyl)-5-methyl-1H-1,2,3-triazole-4-carboxylic acid (Example 13, step 5) and 4-amino-2-cyclohexyl-1,5-dimethyl-1H-pyrazol-3(2H)-one (Intermediate A) analogously to Example 1, step 3.

LC-MS: Rt 4.94 mins; MS m/z 471.3 [M+H]$^+$; Method 10 minLowpHv01

$^1$H NMR (400 MHz, CDCl3) δ 8.36 (1H, s), 7.32 (1H, dd), 7.18 (1H, d), 7.02 (1H, d), 4.06 (1H, mult), 3.24 (3H, s), 2.48 (3H, s), 2.23 (3H, s), 3.05-1.86 (6H, mults), 1.71 (1H, mult), 1.43-1.17 (4H, mults), 0.93 (2H, mults), 0.72 (2H, mults).

Example 15

N-(2-Cyclohexyl-1,5-dimethyl-3-oxo-2,3-dihydro-1H-pyrazol-4-yl)-1-(2-cyclopropyl-4-fluorophenyl)-5-methyl-1H-1,2,3-triazole-4-carboxamide

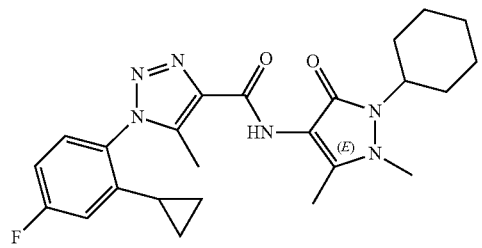 [SMILES: Cc1c(C(=O)Nc2c(C)n(C)n(C3CCCCC3)c2=O)nnn1-c1ccc(F)cc1C1CC1]

Step 1: N-(2-Cyclopropyl-4-fluorophenyl)acetamide

A mixture comprising N-(2-bromo-4-fluorophenyl)acetamide (1 g, 4.31 mmol), cyclopropylboronic acid (0.481 g, 5.60 mmol), tricyclohexylphosphine (0.121 g, 0.431 mmol), potassium phosphate (tribasic) (3.20 g, 15.08 mmol), toluene (10 ml) and water (10 ml) was equally divided between two 10-20 ml microwave tubes. Each reaction tube was sealed, evacuated and filled with nitrogen (3×) and placed in the microwave at 100° C. for 6 hrs. The contents of the vials were combined, diluted with EtOAc and the layers separated. The organic extracts were washed with water (2×), dried over MgSO$_4$, filtered and concentrated under reduced pressure to give the title compound as a brown solid. The product was used crude in the next step.

LC-MS: Rt 0.88 mins; MS m/z 194.3 [M+H]$^+$; Method 2 minLowpHv01

Step 2: 2-Cyclopropyl-4-fluoroaniline

The title compound was prepared from N-(2-cyclopropyl-4-fluorophenyl)acetamide analogously to Example 13 step 3.

LC-MS: Rt 0.65 mins; MS m/z 152.1 [M+H]$^+$; Method 2 minLowpH $^1$H NMR (400 MHz, DMSO-d6) δ 6.70 (1H, tt), 6.60-6.51 (2H, mults), 4.82 (2H, br s), 1.69 (1H, mult), 0.88-0.83 (2H, mults), 0.52-0.48 (2H, mults).

Step 3: 1-Azido-2-cyclopropyl-4-fluorobenzene

The title compound was prepared from 2-cyclopropyl-4-fluoroaniline analogously to Example 13 step 4 to give a brown oil.

Step 4: 1-(2-Cyclopropyl-4-fluorophenyl)-5-methyl-1H-1,2,3-triazole-4-carboxylic acid To a solution of 1-azido-2-cyclopropyl-4-fluorobenzene (237 mg, 1.338 mmol) in MeOH (10 ml) was added methyl 3-oxobutanoate (466 mg, 4.01 mmol) and 5M sodium methoxide (1.338 ml, 6.69 mmol) and the mixture was stirred at 50° C. for 16 hrs. Water (1 ml) was added and stirring continued at 50° C. for 3 hrs. The resulting mixture was concentrated under reduced pressure to remove MeOH. The mixture was washed with EtOAc and organic extracts discarded. To the aqueous layer was added 1M HCl (aq) until acidic and this was extracted with EtOAc (3×). The organic extracts were washed with brine, dried over MgSO$_4$, filtered and concentrated under reduced pressure to give the title compound as a brown oil which was used in the next step without further purification.

LC-MS: Rt 0.97 mins; MS m/z 262.4 [M+H]$^+$; Method 2 minLowpH

Step 5: N-(2-Cyclohexyl-1,5-dimethyl-3-oxo-2,3-dihydro-1H-pyrazol-4-yl)-1-(2-cyclopropyl-4-fluorophenyl)-5-methyl-1H-1,2,3-triazole-4-carboxamide To a solution of oxalyl chloride (0.055 ml, 0.632 mmol) in DCM (5 ml) was added DMF (0.065 ml, 0.842 mmol) dropwise and the mixture was stirred for 1 hr. The resulting mixture was treated with 1-(2-cyclopropyl-4-fluorophenyl)-5-methyl-1H-1,2,3-triazole-4-carboxylic acid (110 mg, 0.421 mmol) and stirring continued at RT for 30 mins. To the reaction mixture was added 4-amino-2-cyclohexyl-1,5-dimethyl-1H-pyrazol-3(2H)-one (Intermediate A) (97 mg, 0.463 mmol) followed by triethylamine (0.176 ml, 1.263 mmol) and stirring continued at RT for 30 mins. The resulting mixture was diluted with DCM, washed with water and eluted though a phase separating cartridge. The organic eluent was collected and concentrated under reduced pressure to give a brown oil. The was absorbed onto silica and purified by chromatography eluting with 0-10% MeOH in TBME. The product fractions were combined, concentrated and dried under reduced pressure to give a pale brown glassy solid. The solid was dissolved in DCM, washed with water, brine and eluted through a phase separating cartridge. The organic eluent was concentrated under reduced pressure to give the title compound as a glassy solid.

LC-MS: Rt 4.84 mins; MS m/z 452.9 [M+H]$^+$; Method 10 minLowpHv01

$^1$H NMR (400 MHz, CDCl3) δ 8.37 (1H, s), 7.24 (1, dd), 7.04 (1H, td), 6.73 (1H, dd), 4.07 (1H, mult), 3.25 (3H, s), 2.47 (3H, s), 2.24 (3H, s), 2.06-1.95 (2H, mults), 1.89 (5H, mults), 1.71 (1H, mult), 1.43-1.18 (3H, mults), 0.95 (2H, mults), 0.71 (2H, mults).

Example 16

N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide

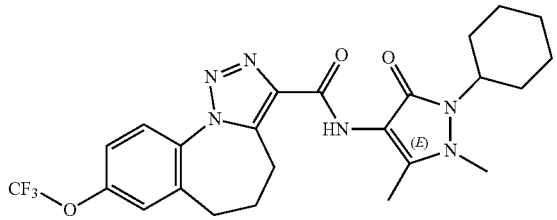 [SMILES: Cc1c(NC(=O)c2nnn3c2CCCc2cc(OC(F)(F)F)ccc2-3)c(=O)n(C2CCCCC2)n1C]

Step 1: 2-Allyl-4-(trifluoromethoxy)aniline

To a solution of 2-bromo-4-(trifluoromethoxy)aniline (75 g, 293 mmol) in DMF (1000 ml) was added Pd(PPh$_3$)$_4$ (13.5 g, 11.7 mmol) and allyltributyltin (116 g, 351 mmol) and the reaction mixture was stirred at 80° C. for 16 h. The mixture was cooled to room temperature and saturated aqueous KF solution was added. The mixture was diluted with ethyl acetate (1500 mL) and washed with 1:1 H$_2$O: saturated aqueous NaCl solution (2×750 mL) and saturated aqueous KF (1×). The aqueous layers were combined and extracted with ethyl acetate (250 mL). The organic extracts were combined, dried over MgSO$_4$, filtered and concentrated under reduced pressure to give the crude product, which was absorbed onto silica and purified by chromatography eluting with 1% ethyl acetate in petroleum ether to give the title compound.

LC-MS: Rt 1.00 mins; MS m/z 218.0 [M+H]$^+$; Method H $^1$H NMR (400 MHz, MeOD) δ 3.27 (2H, dd), 5.07-5.14 (2H, m), 5.92-5.99 (1H, m), 6.72 (1H, dd), 6.88-6.89 (2H, m).

Step 2: N-(2-Allyl-4-(trifluoromethoxy)phenyl)acrylamide

To a solution of 2-allyl-4-(trifluoromethoxy)aniline (17.5 g, 80.6 mmol) in THF (1000 ml), cooled in a dry ice bath to a temperature below −10° C. was added Et$_3$N (8.96 g, 17.3 mmol) and acryloyl chloride (7.98 g, 88.7 mmol). The reaction mixture was allowed to warm to room temperature and stirred for 1 hr. The resulting mixture was concentrated under reduced pressure, dissolved in ethyl acetate, washed with water and brine. The organic portion was dried over Na$_2$SO$_4$, filtered and concentrated in under reduced pressure to give a white solid which was washed with ethyl acetate to give the title compound.

LC-MS: Rt 1.15 mins; MS m/z 272.0 [M+H]$^+$; Method H $^1$H NMR (400 MHz, CDCl$_3$) δ 3.40 (2H, dd), 5.12 (1H, dd), 5.24 (1H, dd), 5.77 (1H, dd), 5.92-5.99 (1H, m), 6.18-6.29 (1H, m), 6.38 (1H, dd), 7.06 (1H, s), 7.15 (1H, dd), 7.36 (1H, s), 8.01 (1H, dd).

Step 3: 7-(Trifluoromethoxy)-1H-benzo[b]azepin-2(5H)-one

To a solution of N-(2-allyl-4-(trifluoromethoxy)phenyl)acrylamide (15 g, 55.3 mmol) in DCM (800 ml) was added Zhan catalyst I (2.0 g, 2.77 mmol) and the mixture was stirred at room temperature for 3 hrs. The resulting mixture was concentrated under reduced pressure to give a crude solid that was recrystallized from ethyl acetate to give the title compound.

LC-MS: Rt 0.95 mins; MS m/z 243.9 [M+H]$^+$; Method H $^1$H NMR (400 MHz, CDCl$_3$) δ 3.37 (2H, dd), 5.97 (1H, dd), 6.60-6.66 (1H, m), 7.02 (1H, s), 7.10-7.13 (2H, m), 9.11 (1H, s).

Step 4: 7-(Trifluoromethoxy)-4,5-dihydro-1H-benzo[b]azepin-2(3H)-one

To a solution of 7-(trifluoromethoxy)-1H-benzo[b]azepin-2(5H)-one (10 g, 41.1 mmol) in 1:1 EtOH:THF (150 ml) was added Pd/C (1.0 g) and the mixture was stirred at room temperature under 30 psi H$_2$ for 3 h. The resulting mixture was filtered and concentrated under reduced pressure to give a crude solid that was recrystallized from ethyl acetate to give the title compound.

LC-MS: Rt 0.98 mins; MS m/z 246.0 [M+H]$^+$; Method H $^1$H NMR (400 MHz, CDCl$_3$) δ 2.22 (2H, q), 2.36 (H, t), 2.80 (2H, t), 7.02-7.03 (1H, m), 7.09 (2H, s), 8.27 (1H, s).

Step 5: 7-(Trifluoromethoxy)-4,5-dihydro-1H-benzo[b]azepine-2(3H)-thione

To a solution of 7-(trifluoromethoxy)-4,5-dihydro-1H-benzo[b]azepin-2(3H)-one (30 g, 122 mmol) in toluene (2000 ml) was added Lawesson's reagent (29.7 g, 73.5 mmol) and the mixture was stirred at 100° C. for 2 hrs. The resulting mixture was cooled to room temperature and concentrated under reduced pressure. The crude product was purified by column chromatography on silica eluting with 5% ethyl acetate in petroleum ether to give the title compound.

LC-MS: Rt 1.04 mins; MS m/z 261.9 [M+H]$^+$; Method H $^1$H NMR (400 MHz, MeOD) δ 2.27-2.34 (2H, m), 2.73-2.79 (4H, m), 7.13-7.15 (1H, m), 7.20-7.22 (2H, m).

Step 6: 2-(Methylthio)-7-(trifluoromethoxy)-4,5-dihydro-3H-benzo[b]azepine

To a solution of 7-(trifluoromethoxy)-4,5-dihydro-1H-benzo[b]azepine-2(3H)-thione (22 g, 84.3 mmol) in acetone (1500 ml) was added KOH (7.1 g, 127 mmol) and MeI (18.1 g, 127 mmol) and the mixture was stirred at RT for 1 h. The resulting mixture was concentrated under reduced pressure and the crude product was dissolved in DCM (1000 mL). The mixture was washed with water, brine, dried over Na₂SO₄, filtered and concentrated under reduced pressure to give a yellow oil. The oil was purified by flash column chromatography on neutral aluminium oxide eluting with hexane to give the title compound.

LC-MS: Rt 1.18 mins; MS m/z 275.9 [M+H]⁺; Method I

¹H NMR (400 MHz, CDCl₃) δ 2.25 (2H, q), 2.32 (2H, t), 2.46 (1H, s), 2.50 (2H, t), 6.99-7.01 (2H, m), 7.09-7.26 (1H, m).

Step 7: (Z)-Ethyl 2-nitro-2-(7-(trifluoromethoxy)-4,5-dihydro-1H-benzo[b]azepin-2(3H)-ylidene)acetate Reference: WO 2011/151361 pages 33 and 34

A mixture of 2-(methylthio)-7-(trifluoromethoxy)-4,5-dihydro-3H-benzo[b]azepine (1 g, 3.63 mmol), ethyl 2-nitroacetate (2.016 ml, 18.16 mmol) and DBU (0.602 ml, 4.00 mmol) was stirred at RT. A bleach scrubbing train was added and the mixture stirred and heated at 40° C. for 72 hrs. The resulting mixture was diluted with EtOAc and washed with water (3×) followed by sat. NaHCO₃(aq) (3×) and brine. The organic extracts were dried over MgSO₄, filtered and concentrated under reduced pressure to give a yellow oil. The oil was absorbed onto silica and purified by chromatography eluting with 0-50% EtOAc. The product fractions were combined, concentrated under reduced pressure and dried under vacuum to give the title compound as a yellow oil.

Step 8: Ethyl 8-(trifluoromethoxy)-5,6-dihydro-4H-benzo[f][1,2,3]triazolo[1,5-a]azepine-3-carboxylate A solution of (Z)-ethyl 2-nitro-2-(7-(trifluoromethoxy)-4,5-dihydro-1H-benzo[b]azepin-2(3H)-ylidene)acetate (892 mg, 2.476 mmol) in glacial acetic acid (50 mL) was cooled in a water bath for 5 mins. To the solution was added zinc (971 mg, 14.85 mmol) portionwise and the mixture was stirred at RT for 4 hrs. Further zinc (486 mg, 7.42 mmol) was added and the mixture was stirred at RT for 16 hrs. To the reaction mixture was added isoamyl nitrite (0.467 mL, 3.47 mmol) and trichloroacetic acid (809 mg, 4.95 mmol) and the mixture was stirred at RT for 48 hrs. The resulting mixture was diluted with DCM and water and the layers separated. The aqueous layer was extracted with DCM (2×) and the organic extracts were combined. The organic extracts were washed with sat. NaHCO₃(aq) (3×), brine, dried over MgSO₄, filtered and concentrated under reduced pressure to give a brown oil. The oil was absorbed on silica and purified by chromatography eluting with 0-50% EtOAc in iso-hexane. The product fractions were combined and concentrated under reduced pressure to give the title compound as a yellow solid.

LC-MS: Rt 1.25 mins; MS m/z 342.3 [M+H]⁺; Method 2 minLowpHv01

¹H NMR (400 MHz, CDCl₃) δ 7.83 (1H, d), 7.34 (1H, dd), 7.27 (1H, br s), 4.49 (2H, q), 3.14 (2H, t), 2.62 (2H, t), 2.40-2.33 (2H, mults), 1.47 (3H, t).

Step 9: 8-(Trifluoromethoxy)-5,6-dihydro-4H-benzo[f][1,2,3]triazolo[1,5-a]azepine-3-carboxylic acid To a solution of ethyl 8-(trifluoromethoxy)-5,6-dihydro-4H-benzo[f][1,2,3]triazolo[1,5-a]azepine-3-carboxylate (384 mg, 1.125 mmol) in THF (5 mL) and methanol (3 mL) was added 2M NaOH (aq) (2.81 mL, 5.63 mmol) and the mixture was stirred at RT for 45 mins. The resulting mixture was concentrated under reduced pressure to give a residue that was partitioned between EtOAc and water. The layers were separated and the aqueous layer was washed with EtOAc. The organic portions were discarded and the aqueous layer was treated with 2M HCl (aq) until acidic. The resltuing solution was extracted with EtOAc and the organic extracts were dried over MgSO₄, filtered and concentrated under reduced pressure to give the title compound as a yellow solid.

LC-MS: Rt 1.07 mins; MS m/z 314.3 [M+H]⁺; Method 2 minLowpHv01

¹H NMR (400 MHz, CDCl3) δ 7.85 (1H, d), 7.38 (1H, d), 7.30 (1H, s), 3.18 (2H, t), 2.66 (2H, t), 2.44-2.37 (2H, mults).

Step 10: N-(2-Cyclohexyl-1,5-dimethyl-3-oxo-2,3-dihydro-1H-pyrazol-4-yl)-8-(trifluoro methoxy)-5,6-dihydro-4H-benzo[f][1,2,3]triazolo[1,5-a]azepine-3-carboxamide To a solution of 8-(trifluoromethoxy)-5,6-dihydro-4H-benzo[f][1,2,3]triazolo[1,5-a]azepine-3-carboxylic acid (169 mg, 0.540 mmol) in dry DCM (2 mL) under nitrogen was added oxalyl chloride (0.052 mL, 0.593 mmol) and DMF (0.084 mL, 1.079 mmol) and the mixture was stirred for 15 mins. 4-Amino-2-cyclohexyl-1,5-dimethyl-1H-pyrazol-3(2H)-one (Intermediate A) (124 mg, 0.593 mmol) was added followed by triethylamine (0.226 mL, 1.619 mmol) and the mixture was stirred at RT for 16 hrs. The resultant mixture was diluted with DCM and water and stirred vigorously. The mixture was passed through a phase separating cartridge and the organic portion was concentrated under reduced pressure to give a yellow oil. The oil was absorbed onto silica and purified by chromatography eluting with 100% TBME. The product fractions were combined and concentrated under reduced pressure to give a glassy solid which was recrystallised from 1:1 diethylether:EtOAc. The resulting crystals were filtered under gravity to give the title compound as a white solid.

LC-MS: Rt 4.99 mins; MS 505.3 m/z [M+H]⁺; Method 10 minLowpHv01

¹H NMR (400 MHz, DMSO-d6) δ 9.31 (1H, s), 7.88 (1H, d), 7.64 (1H, br s), 7.56 (1H, br d), 3.93 (1H, tt), 3.22 (3H, s), 3.07 (2H, t), 2.64 (2H, t), 2.23 (2H, t), 2.07 (3H,s), 2.02-1.97 (2H, mults), 1.80 (2H, br d), 1.70-1.61 (3H, mults), 1.32 (2H, q), 1.21-1.15 (1H, mult).

Example 17

N-(2-Cyclohexyl-1,5-dimethyl-3-oxo-2,3-dihydro-1H-pyrazol-4-yl)-1-(4-methoxyphenyl)-5-methyl-1H-1,2,3-triazole-4-carboxamide

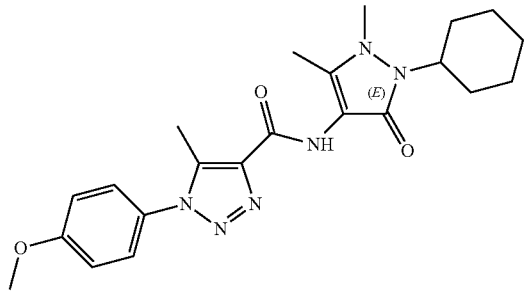 [SMILES: COc1ccc(-n2nnc(C(=O)Nc3c(C)n(C)n(C4CCCCC4)c3=O)c2C)cc1]

Step 1: N-(2-Cyclohexyl-1,5-dimethyl-3-oxo-2,3-dihydro-1H-pyrazol-4-yl)-1-(4-methoxyphenyl)-5-methyl-1H-1,2,3-triazole-4-carboxamide To a vial was added 1-(4-methoxyphenyl)-5-methyl-1H-1,2,3-triazole-4-carboxylic acid (0.040 g, 0.170 mmol) and a solution of Ghosez reagent (0.047 ml, 0.340 mmol) in DCM (0.95 ml). The mixture was sonicated and heated to aid dissolution. The vial was placed on the IKA shaker for 4 hours. To this mixture was added a solution of 4-amino-2-cyclohexyl-1,5-dimethyl-1H-pyrazol-3(2H)-one (Intermediate A) (10.043 g, 0.204 mmol) and N,N-diisopropylethylamine (0.030 ml, 0.170 mmol) in DCM (0.97 ml) and the vial was shaken for 16 hrs. A few drops of MeOH were added and the solvent was removed using a Genevac HT-4X evaporator. The crude mixture was purified by reverse phase chromatography and the product fraction was concentrated using a Genevac HT-4X evaporator. The crude product was dissolved in MeOH (1 ml) and eluted through a SiCO$_3$ cartridge using MeOH as the eluent. The collected eluent was concentrated to give the title compound.

LC-MS: Rt 0.98 mins; MS m/z 425.3 [M+H]$^+$; Method 2 minLowpHv02

$^1$H NMR (400 MHz, CDCl$_3$) δ 8.40 (1H, br s), 7.37 (2H, dt), 7.07 (2H, dt), 4.06 (1H, mult), 3.90 (3H, s), 3.24 (3H, s), 2.58 (3H, s), 2.22 (3H, s), 2.06-1.92 (2H, mults), 1.87 (4H, br d), 1.70 (1H, br d), 1.45-1.30 (2H, mults), 1.28-1.16 (1H, mult).

PREPARATION OF INTERMEDIATES

Intermediate A

4-Amino-2-cyclohexyl-1,5-dimethyl-1H-pyrazol-3(2H)-one

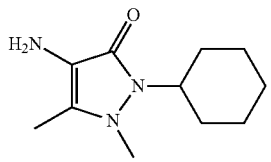

Step 1: 2-Cyclohexyl-5-methyl-1H-pyrazol-3(2H)-one

Cyclohexylhydrazine hydrochloride (700 g, 4643 mmol) was added to a stirred solution of DCM (3000 ml) and ice cold 2M NaOH solution (1778 mL, 3556 mmol) and this was stirred for 10 minutes at RT. The phases were separated and the aqueous layer was washed with DCM (4×2000 ml). The combined organic extracts were dried over anhydrous sodium sulphate, filtered and concentrated under reduced pressure to give a yellow solid. The solid cyclohexylhydrazine (406 g, 3556 mmol) was dissolved in water (1300 mL) and acetic acid (1300 mL) and treated with ethyl acetoacetate (450 mL, 3556 mmol). The reaction mixture was heated to 85° C. and stirred for 1 hour. The resulting mixture was concentrated to dryness under reduced pressure and the residue was dissolved in DCM (3000 ml) and water (1000 ml). The mixture was neutralized with 2M potassium carbonate to pH>9, the resulting phases were separated and the organic extract was washed with brine (1×2 L). The first aqueous layer was saturated with sodium chloride and both aqueous phases washed with DCM (4×2 L). The combined organic extracts were dried over anhydrous sodium sulfate, filtered and concentrated under reduced pressure to give a beige solid. The crude product was ground to a powder, TBME (2000 ml) was added and the mixture was stirred at 50° C. for 1 hour, followed by 1 hour at room temperature. The resulting solid was collected by filtration, washed with TBME (4×500 ml) and dried under vacuum at 45° C. for 16 hours to yield the title compound as off-white crystals.

LC-MS: Rt 0.63 mins; MS m/z 181.1 [M+H]$^+$; Method C $^1$H NMR (400 MHz, DMSO-d6) δ 10.62 (1H, br s), 5.06 (1H, s), 3.89 (1H, mult), 1.98 (3H, s), 1.81-1.55 (7H, mults), 1.36-1.22 (2H, mults), 1.18-1.05 (1H, mult).

Step 2: 2-Cyclohexyl-1,5-dimethyl-1H-pyrazol-3(2H)-one

A suspension of 2-cyclohexyl-5-methyl-1H-pyrazol-3(2H)-one (525 g, 2834 mmol) in N,N-dimethylformamide (2200 mL) was heated to 40° C. and methyl iodide (532 mL, 8502 mmol) was added. The reaction mixture was heated to 70° C. for 20 h. Further methyl iodide (177 mL, 2834 mmol) was added and the mixture was stirred at 75° C. for 3.5 hours, then 80° C. for 20 hours. The resulting mixture was concentrated under reduced pressure and the residue was triturated with TBME (2000 ml). The product was collected by filtration, washing with TBME (5×500 ml) to give a solid which was suspended in DCM (2500 ml) and water (500 ml) and neutralized with 2M potassium carbonate solution (1700 ml) to pH>9. The phases were separated and the aqueous layer was extracted with DCM (3×500 ml). The organic extracts were washed with brine (1000 ml) and concentrated under reduced pressure. The resulting residue was dissolved in ethyl acetate (2000 ml), dried over anhydrous sodium sulfate and filtered through 200 g of silica gel (40-63 μm), washing with ethyl acetate/methanol 9:1 (7×300 ml). The filtrate was concentrated under reduced pressure and to give the title compound as a brown oil.

LC-MS: Rt 0.67 mins; MS m/z 195.1 [M+H]$^+$; Method C $^1$H NMR (400 MHz, DMSO-d6) δ 5.02 (1H, s), 3.84 (1H, tt), 3.14 (3H, s), 2.06 (3H, s), 1.98-1.86 (2H, mults), 1.78-1.53 (5H, mults), 1.33-1.20 (2H, mults), 1.18-1.04 (1H, mult).

Step 3: 2-Cyclohexyl-1,5-dimethyl-4-nitro-1H-pyrazol-3(2H)-one

To trifluoroacetic acid (1940 mL) cooled to −15° C. was added 2-cyclohexyl-1,5-dimethyl-1H-pyrazol-3(2H)-one (535 g, 2231 mmol) and the reaction mixture was allowed to warm to 0° C. Nitric acid 90% (211 mL, 4461 mmol) was added dropwise over 90 minutes maintaining the temperature below 15° C. and the resulting mixture was stirred for 30 minutes at 10° C. The product mixture was slowly poured into ice water (8 L) and stirred for 30 minutes. The solid was collected by filtration and washed with water (2×2 L), saturated sodium bicarbonate solution (1×2 L), water (2×2 L), TBME (3×2 L) and heptane (2×2 L). The solid was dried in the vacuum oven to yield the title compound as a beige powder.

LC-MS: Rt 0.65 mins; MS m/z 240.1 [M+H]$^+$; Method C $^1$H NMR (400 MHz, DMSO-d6) δ 4.06 (1H, tt), 3.61 (3H, s), 2.57 (3H, t), 2.15-2.03 (2H, mults), 1.81-1.65 (4H, mults), 1.64-1.55 (1H, mult), 1.38-1.24 (2H, mults), 1.19-1.06 (1H, mult).

Step 4: 4-Amino-2-cyclohexyl-1,5-dimethyl-1H-pyrazol-3(2H)-one

To 2-cyclohexyl-1,5-dimethyl-4-nitro-1H-pyrazol-3(2H)-one (415 g, 1.73 mol) in MeOH (4500 ml) and THF (4500 ml) was added 10% Pd/C (70 g) and the reaction mixture was hydrogenated at 0.1 bar and RT for 57.5 hrs. The resulting mixture was filtered through a pressure strainer and washed with methanol (1×1 L) and THF (2×1 L). The filtrate was concentrated under reduced pressure to give a dark red oil. The oil was dissolved immediately in TBME (4 L), concentrated under reduced pressure to ca. 2 L and seeded (100 mg). The suspension was stirred for 2 hrs at RT and cooled in an ice bath for 1 hr. The solid was collected by filtration and washed with ice cold TBME in portionwise until the filtrate was colourless and dried under vacuum to give the title compound as yellow/pale orange crystals.

LC-MS: Rt 0.55 mins; MS m/z 210.1 [M+H]⁺; Method C
¹H NMR (400 MHz, DMSO-d6) δ 3.68 (1H, tt), 3.53 (2H, br s), 2.77 (3H, s), 1.96-1.83 (2H, mults), 1.92 (3H, s), 1.78-1.69 (2H, mults), 1.64-1.53 (3H, mults), 1.33-1.19 (2H, mults), 1.17-1.04 (1H, mult).

Intermediate B

4-Amino-2-(2-fluorophenyl)-1,5-dimethyl-1H-pyrazol-3(2H)-one

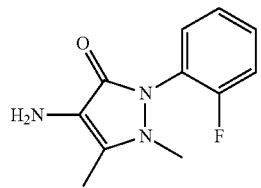 [SMILES: Cc1c(N)c(=O)n(-c2ccccc2F)n1C]

Step 1: 2-(2-Fluorophenyl)-5-methyl-1H-pyrazol-3(2H)-one A stirred suspension of 2-fluorophenylhydrazine hydrochloride (1000 g, 5535 mmol) in acetic acid (1000 ml) and water (1000 ml) was heated at 45° C. Ethylacetoacetate (700 ml) was added dropwise over 30 mins and this was stirred at 88° C. for 2 hr. The resulting mixture was cooled to 5° C. and poured onto ice (3000 g) and DCM (4500 ml). 30% NaOH (aq) (2400 ml) was added and the mixture was stirred for 15 mins, then separated and extracted with DCM (1500 ml). The organic extracts were washed with 1M NaOH (aq) (1500 ml). The aqueous phases were combined and ice (1500 g) and DCM (3600 ml) were added. To the stirred mixture was added 32% HCl (aq) (2400 ml) until the pH was adjusted to pH 1-2. The biphasic mixture was separated, extracted with DCM (1500 ml) and the organic extracts washed with brine/water 4:1 (2000 ml), dried over MgSO₄ and evaporated to dryness to give a dark solid. To a stirred solution of the crude product in DCM (2000 ml) was added silica gel (350 g). This was filtered and the filtrate was evaporated. Purification by chromatography with MeOH in EtOAc gave the title compound as a light yellow solid.

LC-MS: Rt 0.54 mins; MS m/z 193.1 [M+H]⁺; Method B
¹H NMR (400 MHz, DMSO-d6) δ 11.20 (1H, br s), 7.48-7.40 (2H, mults), 7.36 (1H, td), 7.29 (1H, td), 5.31 (1H, br s), 2.10 (3H, s).

Step 2: 2-(2-Fluorophenyl)-1,5-dimethyl-1H-pyrazol-3(2H)-one To a solution of 2-(2-fluorophenyl)-5-methyl-1H-pyrazol-3(2H)-one (500 g, 2602 mmol) in THF (2500 ml) heated to 58° C. was added iodomethane (163 ml) dropwise over 15 mins and the mixture was stirred at 65° C. for 30 mins. K₂CO₃ (198 g) was added over 20 mins and stirred for 16 hrs. Further iodomethane (16.3 ml) was added and stirring continued for 1 hr. The resulting mixture was cooled to 0° C., filtered and washed with THF (50 ml). The filtrate was evaporated to dryness and purified by column chromatography, eluting with EtOAc/Heptane to give the title compound as a red solid.

LC-MS: Rt 0.54 mins; MS m/z 207.1 [M+H]⁺; Method B
¹H NMR (400 MHz, DMSO-d6) δ 7.51-7.44 (1H, mult), 7.42-7.28 (3H, mults), 5.19 (1H, s), 3.00 (3H, s), 2.19 (3H, s).

Step 3: 2-(2-Fluorophenyl)-1,5-dimethyl-4-nitro-1H-pyrazol-3(2H)-one 2-(2-Fluorophenyl)-1,5-dimethyl-1H-pyrazol-3(2H)-one (260 g, 1261 mmol) in TFA (1040 ml) was cooled to −10° C. and stirred for 30 mins. To the mixture was added fuming nitric acid (84 ml) dropwise and this was stirred for 15 mins under cooling then at RT for 1 hr. The resulting mixture was poured onto a mixture of ice (1500 ml), water (1000 ml) and TBME (2500 ml) and stirred until the ice melted, then at RT for 1 hr. The mixture was filtered, washed with water (200 ml) and TBME (1000 ml). The collected crystals were dried to give the title compound as red-brown crystals.

LC-MS: Rt 0.53 mins; MS m/z 252.1 [M+H]⁺; Method B
¹H NMR (400 MHz, DMSO-d6) δ 7.68-7.61 (1H, mult), 7.58-7.47 (2H, mults), 7.41 (1H, t), 3.37 (3H, s), 2.69 (3H, s).

Step 4: 4-Amino-2-(2-fluorophenyl)-1,5-dimethyl-1H-pyrazol-3(2H)-one 2-(2-Fluorophenyl)-1,5-dimethyl-4-nitro-1H-pyrazol-3(2H)-one (208 g, 828 mmol) and 10% Pd/C (25 g, 235 mmol) in MeOH (3000 ml) was subjected to hydrogenation over 98 hrs at 0.1 bar at RT. The resulting mixture was filtered over a pad of Celite® (filter material), washed with MeOH (1000 ml) and the filtrate was evaporated to dryness. To the solid was added DCM (300 ml) and this was heated at 65° C., followed by addition of toluene (900 ml). The DCM was removed under reduced pressure and the resulting mixture was allowed to cool to RT with stirring and left to stand at RT overnight. The mixture was filtered, washing with 1:1 toluene:heptane (200 ml) and heptane (800 ml) and dried under v to give the title compound as light yellow crystals.

LC-MS: Rt 0.47 mins; MS m/z 222.1 [M+H]⁺; Method MP
¹H NMR (400 MHz, DMSO-d6) δ 7.46-7.41 (1H, mult), 7.37 (3H, t), 7.35-7.27 (2H, mults), 2.68 (3H, s), 2.07 (3H,s).

Intermediate C

4-Amino-2-cyclohexyl-1-methyl-d₃,5-methyl-1H-pyrazol-3(2H)-one

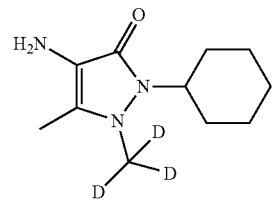 [SMILES: [2H]C([2H])([2H])n1c(C)c(N)c(=O)n1C1CCCCC1]

Step 1: 2-Cyclohexyl-1-methyl-d₃,5-methyl-1H-pyrazol-3(2H)-one 2-Cyclohexyl-5-methyl-1H-pyrazol-3(2H)-one (Intermediate A, step 1) (1 g, 5.55 mmol) was slurried in DMF (5 ml) and heated to 40° C. under an atmosphere of nitrogen. Iodomethane-d₃ (1.381 mL, 22.19 mmol) was added, nitrogen flow turned off and the mixture heated at 70° C. for 16 hrs. The resulting mixture was cooled to room temperature. DCM (20 ml) was added, followed by lithium chloride (5% w/v, 25 ml). The resulting layers were separated and the organic extracts washed with brine (20 ml). The aqueous washes were combined and re-extracted with DCM (2×10 ml). The combined organic extracts were dried over MgSO₄. The desiccant was filtered off and the filtrate concentrated under reduced pressure to give a brown oil. The oil was absorbed onto silica and purified by chromatography eluting with 0-10% MeOH in DCM. The product fractions were combined and concentrated under reduce pressure to give the title compound as a brown oil.

LC-MS: Rt 0.74 mins; MS m/z 198.4 [M+H]+; Method 2 minLowpHv01

$^1$H NMR (400 MHz, DMSO-d6) δ 5.30 (1H, s), 4.02 (1H, m), 2.15 (3H, s), 1.97 (2H, m), 1.78 (2H, m), 1.66 (3H, m), 1.33 (2H, m), 1.15 (1H, m).

Step 2: 2-Cyclohexyl-1-methyl-d$_3$, 5-methyl-4-nitro-1H-pyrazol-3(2H)-one 2-Cyclohexyl-1-methyl-d$_3$,5-methyl-1H-pyrazol-3(2H)-one (690 mg, 3.50 mmol) was dissolved in TFA (5389 μl, 69.9 mmol) and 90% nitric acid (347 μl, 6.99 mmol) was added dropwise under ice cooling keeping the temperature ~5° C. The mixture was stirred at RT for 30 mins and then poured into water (30 ml) and extracted with DCM (30 ml). The organic extracts were washed with brine, dried over MgSO$_4$, filtered and concentrated under reduced pressure to give the title compound.

LC-MS: Rt 0.75 mins; MS m/z 243.3 [M+H]+; Method 2 minLowpHv01

$^1$H NMR (400 MHz, DMSO-d6) δ 4.07 (1H, m), 2.59 (3H, s), 2.1 (2H, m), 1.78 (2H, m), 1.67 (3H, m), 1.33 (2H, m), 1.16 (1H, m).

Step 3: 4-Amino-2-cyclohexyl-1-methyl-d$_3$,5-methyl-1H-pyrazol-3(2H)-one To a solution of 2-cyclohexyl-1-methyl-d$_3$, 5-methyl-4-nitro-1H-pyrazol-3(2H)-one (430 mg, 1.775 mmol) in ethanol (5 mL) was added ammonium chloride (356 mg, 6.66 mmol), iron (347 mg, 6.21 mmol) and water (1.25 mL), followed by conc. HCl (0.054 mL, 1.775 mmol). The mixture was stirred at 90° C. for 1.5 hrs and then cooled to room temperature and stirred at RT for 16 hrs. The resulting mixture was filtered, taken to pH8 by the addition of 1M NaOH (aq) and extracted with DCM. The organic extracts were washed with brine, dried over MgSO$_4$, filtered and concentrated under reduced pressure. The crude material was absorbed onto silica and purified by chromatography eluting with 0-20% MeOH in TBME. The product fractions were combined, concentrated under reduced pressure and dried in the vacuum oven to give the title compound as a pale yellow solid.

LC-MS: Rt 0.50 mins; MS m/z 213.4 [M+H]+; Method 2 minLowpHv01

$^1$H NMR (400 MHz, CDCl$_3$) δ 3.86 (1H, m), 2.01 (3H, s), 1.92 (2H, m), 1.83 (4H, m), 1.65 (1H, m), 1.32 (2H, m), 1.19 (1H, m).

The invention claimed is:

1. A method of treating pulmonary arterial hypertension, fibrosis, rheumatoid arthritis, fracture healing, glaucoma, hereditary hemorrhagic telangiectasia, proteinuria, wound healing, COPD, or asthma, in a subject suffering from any one of pulmonary arterial hypertension, fibrosis, rheumatoid arthritis, fracture healing, glaucoma, hereditary hemorrhagic telangiectasia, proteinuria, wound healing, COPD, or asthma comprising: administering to said subject a therapeutically effective amount of a compound of formula (I):

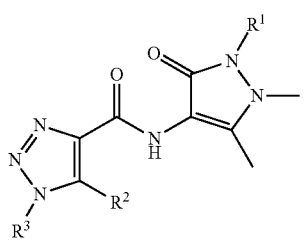

(I)

or a pharmaceutically acceptable salt thereof, wherein
$R^1$ is (C$_3$-C$_6$)alkyl or (C$_3$-C$_6$)cycloalkyl;
$R^2$ is methyl;
$R^3$ is

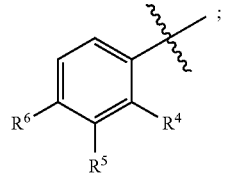

$R^4$ and $R^5$ are independently selected from hydrogen, halo, (C$_3$-C$_6$)cycloalkyl, (C$_1$-C$_4$)alkyl, halo(C$_1$-C$_4$)alkyl, (C$_1$-C$_4$)alkoxy, halo(C$_1$-C$_4$)alkoxy or —(C$_1$-C$_2$)alkyl(C$_1$-C$_2$)alkoxy; or $R^2$ and $R^4$ may be taken together with the carbon atoms to which they are attached to form an azepine ring and $R^5$ is H;

$R^6$ is halo, (C$_3$-C$_6$)cycloalkyl, (C$_1$-C$_4$)alkyl, halo(C$_1$-C$_4$)alkyl, (C$_1$-C$_4$)alkoxy, halo(C$_1$-C$_4$)alkoxy or —(C$_1$-C$_2$)alkyl(C$_1$-C$_2$)alkoxy;

OR $R^1$ is 2-fluorophenyl;
$R^2$ is methyl; and
$R^3$ is phenyl, substituted with one or two substituents independently selected from chloro and cyclopropyl.

2. The method according to claim 1 or a pharmaceutically acceptable salt thereof, wherein $R^1$ is iso-propyl, cyclobutyl or cyclohexyl.

3. The method according to claim 1 or a pharmaceutically acceptable salt thereof, wherein $R^1$ is cyclohexyl.

4. The method according to claim 1 or a pharmaceutically acceptable salt thereof, wherein $R^3$ is

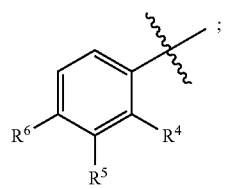

$R^4$ and $R^6$ are independently selected from chloro, fluoro, cyclopropyl, methyl, methoxy, trifluoromethoxy, trifluoromethyl; and $R^5$ is hydrogen.

5. The method according to claim 1 or a pharmaceutically acceptable salt thereof, wherein $R^3$ is

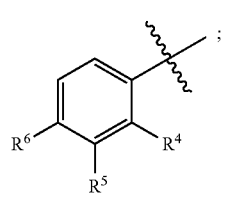

$R^4$ and $R^6$ are independently selected from chloro and cyclopropyl; and $R^5$ is hydrogen.

6. The method according to claim 1 which is selected from the group consisting of:

1-(2-Chloro-4-methoxyphenyl)-N-(2-cyclohexyl-1,5-dimethyl-3-oxo-2,3-dihydro-1H-pyrazol-4-yl)-5-methyl-1H-1,2,3-triazole-4-carboxamide;
N-(2-Cyclohexyl-1,5-dimethyl-3-oxo-2,3-dihydro-1H-pyrazol-4-yl)-1-(2,4-dichlorophenyl)-5-methyl-1H-1,2,3-triazole-4-carboxamide;
N-(2-Cyclohexyl-1,5-dimethyl-3-oxo-2,3-dihydro-1H-pyrazol-4-yl)-1-(4-methoxy-2-(trifluoromethyl)phenyl)-5-methyl-1H-1,2,3-triazole-4-carboxamide;
N-(2-Cyclohexyl-1,5-dimethyl-3-oxo-2,3-dihydro-1H-pyrazol-4-yl)-1-(4-methoxy-3-methylphenyl)-5-methyl-1H-1,2,3-triazole-4-carboxamide;
1-(2-Chloro-4-(trifluoromethoxy)phenyl)-N-(2-cyclohexyl-1,5-dimethyl-3-oxo-2,3-dihydro-1H-pyrazol-4-yl)-5-methyl-1H-1,2,3-triazole-4-carboxamide;
1-(4-Chlorophenyl)-N-(2-cyclohexyl-1,5-dimethyl-3-oxo-2,3-dihydro-1H-pyrazol-4-yl)-5-methyl-1H-1,2,3-triazole-4-carboxamide,
1-(2,4-Dichlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide;
1-(4-Chlorophenyl)-N-(2-(2-fluorophenyl)-1,5-dimethyl-3-oxo-2,3-dihydro-1H-pyrazol-4-yl)-5-methyl-1H-1,2,3-triazole-4-carboxamide,
1-(2-Chloro-4-(trifluoromethoxy)phenyl)-N-(2-(2-fluorophenyl)-1,5-dimethyl-3-oxo-2,3-dihydro-1H-pyrazol-4-yl)-5-methyl-1H-1,2,3-triazole-4-carboxamide;
1-(2-Chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide;
1-(2-Chloro-4-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide;
1-(2-Chloro-4-cyclopropylphenyl)-N-(2-cyclohexyl-1-methyl-d$_3$,5-methyl-3-oxo-2,3-dihydro-1H-pyrazol-4-yl)-5-methyl-1H-1,2,3-triazole-4-carboxamide;
1-(4-Chloro-2-cyclopropylphenyl)-N-(2-(2-fluorophenyl)-1,5-dimethyl-3-oxo-2,3-dihydro-1H-pyrazol-4-yl)-5-methyl-1H-1,2,3-triazole-4-carboxamide;
1-(4-Chloro-2-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide;
N-(2-Cyclohexyl-1,5-dimethyl-3-oxo-2,3-dihydro-1H-pyrazol-4-yl)-1-(2-cyclopropyl-4-fluorophenyl)-5-methyl-1H-1,2,3-triazole-4-carboxamide;
N-(2-Cyclohexyl-1,5-dimethyl-3-oxo-2,3-dihydro-1H-pyrazol-4-yl)-8-(trifluoromethoxy)-5,6-dihydro-4H-benzo[f][1,2,3]triazolo[1,5-a]azepine-3-carboxamide; and
N-(2-Cyclohexyl-1,5-dimethyl-3-oxo-2,3-dihydro-1H-pyrazol-4-yl)-1-(4-methoxyphenyl)-5-methyl-1H-1,2,3-triazole-4-carboxamide,
or a pharmaceutically acceptable salt thereof.

7. The method according to claim 1 wherein the disease or disorder is selected from pulmonary arterial hypertension (PAH), Fibrosis, Rheumatoid Arthritis, and Fracture healing.

8. The method according to claim 1 wherein the disease or disorder is selected from glaucoma, hereditary hemorrhagic telangiectasia (HHT), proteinuria, wound healing, COPD and asthma.

9. The method according to claim 1, wherein the compound is 1-(2-chloro-4-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide having the following formula:

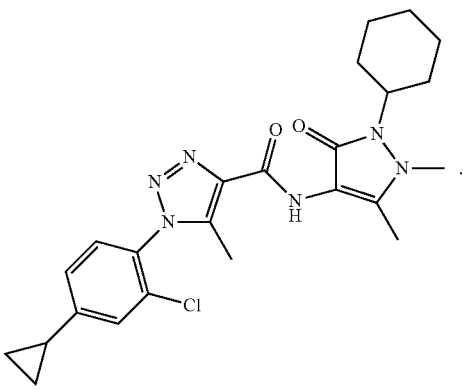 [SMILES: Cc1c(C(=O)Nc2c(C)n(C)n(C3CCCCC3)c2=O)nnn1-c1ccc(C2CC2)cc1Cl]

10. The method according to claim 1, wherein the compound is 1-(2-Chloro-4-methoxyphenyl)-N-(2-cyclohexyl-1,5-dimethyl-3-oxo-2,3-dihydro-1H-pyrazol-4-yl)-5-methyl-1H-1,2,3-triazole-4-carboxamide having the following formula:

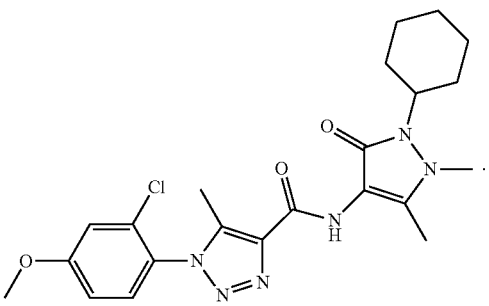

11. The method according to claim 1, wherein the compound is 1-(4-Chloro-2-cyclopropylphenyl)-N-(2-cyclohexyl-1,5-dimethyl-3-oxo-2,3-dihydro-1H-pyrazol-4-yl)-5-methyl-1H-1,2,3-triazole-4-carboxamide having the following formula:

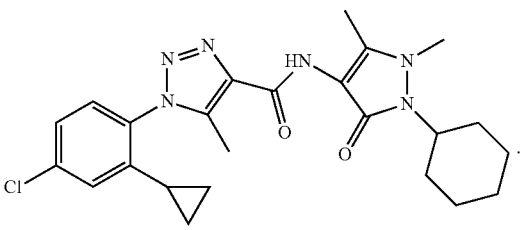 [SMILES: Cc1c(C(=O)Nc2c(C)n(C)n(C3CCCCC3)c2=O)nnn1-c1ccc(Cl)cc1C1CC1]

* * * * *